United States Patent [19]

Platz et al.

[11] 4,259,235

[45] Mar. 31, 1981

[54] TRICYCLIC NITROGENOUS COMPOUNDS HAVING STRING PLANT GROWTH REGULATING PROPERTIES

[75] Inventors: Rolf Platz, Mannheim; Werner Fuchs, Ludwigshafen; Norbert Rieber, Mannheim; Johann Jung; Bruno Wuerzer, both of Limburgerhof, all of Fed. Rep. of Germany

[73] Assignee: BASF Aktiengesellschaft, Fed. Rep. of Germany

[21] Appl. No.: 941,010

[22] Filed: Sep. 11, 1978

[30] Foreign Application Priority Data

Sep. 19, 1977 [DE] Fed. Rep. of Germany ....... 2742034

[51] Int. Cl.$^3$ ................. C07C 107/04; C07C 229/00; C07C 261/08; C07D 261/20
[52] U.S. Cl. ................. 260/152; 71/64 A; 71/86; 71/88; 71/90; 71/92; 260/239 A; 260/239 E; 260/348.44; 260/348.53; 546/262; 548/162; 548/190; 548/218; 548/242; 548/258; 548/259; 548/303; 548/304; 548/370; 549/31; 549/38
[58] Field of Search .......... 260/302 F, 239 A, 239 E, 260/307 R, 307 D, 307 F, 152, 308 R, 308 B, 348.44, 348.53, 348.11, 239 AR; 548/303, 304, 162, 190, 218, 242, 258, 259, 370; 546/262; 549/31, 38

[56] References Cited

U.S. PATENT DOCUMENTS

| 3,573,281 | 3/1971 | Nehring | 260/307 F X |
| 3,953,444 | 4/1976 | Singh et al. | 260/250 AC |

OTHER PUBLICATIONS

Nelsen et al., J. Amer. Chem. Soc., vol. 96, pp. 1788 to 1793 (1974).
Rieber et al., J. Amer. Chem. Soc., vol. 91, pp. 5668 and 5669 (1969).

*Primary Examiner*—Floyd D. Higel
*Attorney, Agent, or Firm*—Keil & Witherspoon

[57] ABSTRACT

Tricyclic nitrogenous compounds having strong plant growth regulating properties are disclosed. The compounds display the general formula

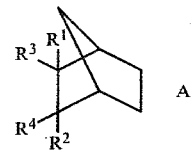

wherein A is one of several nitrogen-containing radicals, $R^1$, $R^2$, $R^3$ and $R^4$ are selected from various recited aliphatic, aryl, araliphatic and heterocyclic groups. $R^3$ and $R^4$ may also together form one of a number of nitrogen, sulfur and oxygen containing radicals. These compounds have a variety of uses, including the reduction of plant growth height without harm to the plant.

2 Claims, No Drawings

TRICYCLIC NITROGENOUS COMPOUNDS HAVING STRING PLANT GROWTH REGULATING PROPERTIES

The present invention relates to new and valuable polycyclic compounds, processes for their manufacture, crop protection agents containing these compounds, and their use as crop protection agents.

We have found that compounds of the formula

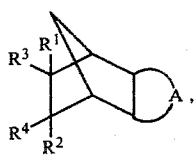

where $R^3$ and $R^4$ are individual radicals or together denote the radical $(B)_n$, A denotes the radicals $-N=N-$,

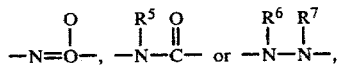

B denotes 1 or 3 hetero atoms (O, N, S) or carbon atoms, viz., the radicals

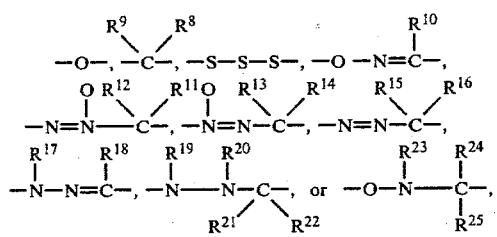

B may also, when A is

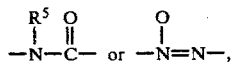

denote the radicals

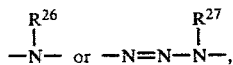

n is one of the integers 0 and 1, $R^1$ to $R^{27}$ are identical or different and each denotes hydrogen, or alkyl, alkenyl or alkynyl of 1 to 30 carbon atoms, preferably alkyl of 1 to 18 carbon atoms which may be cyclic or acyclic and linear or branched, phenyl or naphthyl, or a more highly condensed aromatic radical, a heterocyclic radical with one or several hetero atoms (O, N, S), or aralkyl, the aromatic radical if desired being replaced by a heterocycle with the proviso that $R^3$ and $R^4$ are not hydrogen and do not simultaneously denote alkyl; the abovementioned radicals, apart from hydrogen, may be mono- or polysubstituted by halogen (F, Cl, Br, I), pseudo-halogen (e.g., CN, OCN, $N_3$, SCN), $-OH$, $-SH$, $-NO_2$, $-NH_2$, $-NO$, $=N-OH$, $=O$, $=N-OAlk(Ar)$, $=S$, $=NH$,

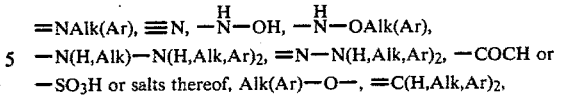

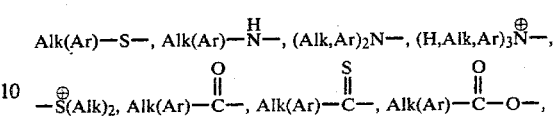

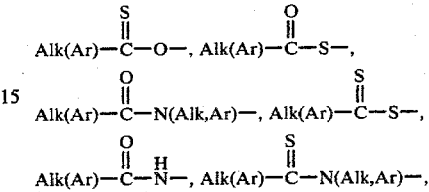

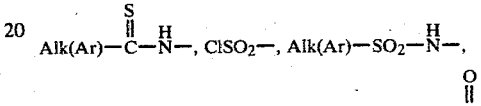

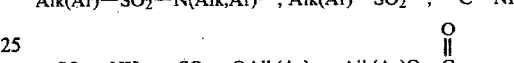

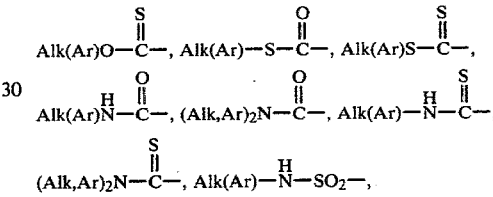

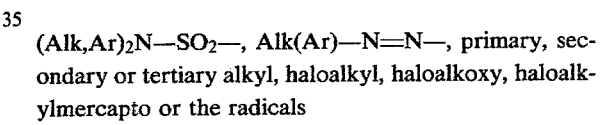

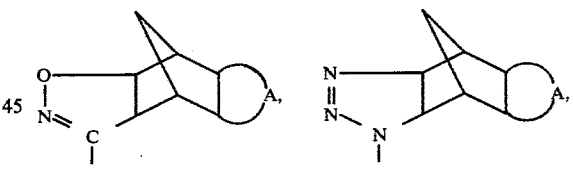

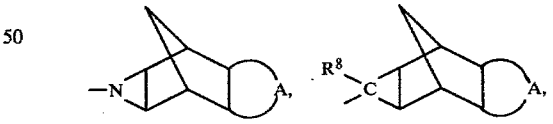

$(Alk,Ar)_2N-SO_2-$, $Alk(Ar)-N=N-$, primary, secondary or tertiary alkyl, haloalkyl, haloalkoxy, haloalkylmercapto or the radicals

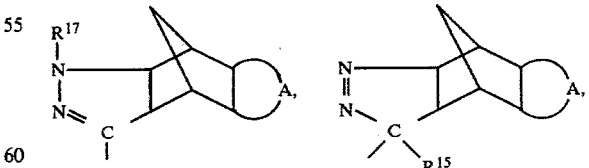

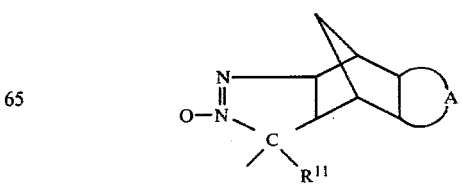

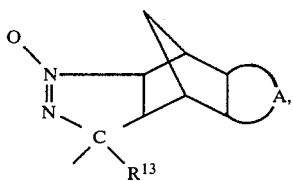

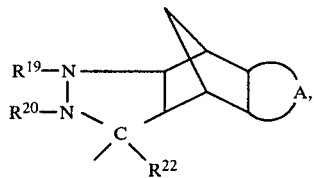

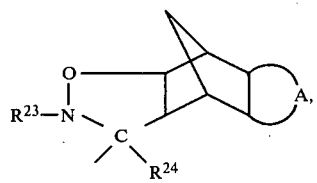

Alk denoting alkyl and Ar an aromatic radical which may also be substituted as given above, further, $R^1$ to $R^7$ are identical or different and each denotes halogen (F, Cl, Br, I) or pseudohalogen (CN, SCN, OCN, $N_3$), —OH —SH, —$NO_2$, —$NH_2$, —NO, —$\overset{H}{N}$—OH, —$\overset{H}{N}$—OAlk(Ar), —N(H,Alk)—N(H, Alk,Ar)$_2$, —COOH or —$SO_3H$ or salts thereof, $SO_2Cl$, Alk(Ar)—O—, Alk(Ar)—S—, Alk(Ar)—$\overset{H}{N}$—, (Alk,Ar)$_2$N—, (H,Alk,Ar)$_3\overset{\oplus}{N}$—, —$\overset{\oplus}{S}$(Alk)$_2$, Alk(Ar)—$\overset{O}{\overset{\|}{C}}$—, Alk(Ar)—$\overset{S}{\overset{\|}{C}}$—, Alk(Ar)—$\overset{O}{\overset{\|}{C}}$—O—, Alk(Ar)—$\overset{S}{\overset{\|}{C}}$—O—, Alk(Ar)—$\overset{O}{\overset{\|}{C}}$—S—, Alk(Ar)—$\overset{O}{\overset{\|}{C}}$—N(Alk,Ar)—, Alk(Ar)—$\overset{S}{\overset{\|}{C}}$—S—, Alk(Ar)—$\overset{O}{\overset{\|}{C}}$—$\overset{H}{N}$—, (Alk(Ar)—$\overset{S}{\overset{\|}{C}}$—N(Alk,Ar)—, Alk(Ar)—$\overset{S}{\overset{\|}{C}}$—$\overset{H}{N}$—, Alk(Ar)—$SO_2$—$\overset{H}{N}$—, Alk(Ar)—$SO_2$—N(Alk,Ar)—, Alk(Ar)—$SO_2$—, —$\overset{O}{\overset{\|}{C}}$—$NH_2$, —$SO_2$—$NH_2$, (Alk,Ar—O—)$_2\overset{O}{\overset{\|}{P}}$—O—, (Alk,Ar—O—)$_2\overset{O}{\overset{\|}{P}}$—$\overset{H}{N}$—, (Alk,Ar—O—)$_2\overset{S}{\overset{\|}{P}}$—O—, (Alk,Ar—O—)$_2\overset{S}{\overset{\|}{P}}$—$\overset{H}{N}$—, (Alk,Ar—O—) (Alk,Ar)$\overset{O}{\overset{\|}{P}}$—O—, (Alk,Ar—O—) (Alk,Ar)$\overset{O}{\overset{\|}{P}}$—$\overset{H}{N}$—, (Alk,Ar—O—)(Alk,Ar)$\overset{S}{\overset{\|}{P}}$—O—, (Alk,Ar—O—)(Alk,Ar)$\overset{S}{\overset{\|}{P}}$—$\overset{H}{N}$—, Alk(Ar)O—$\overset{O}{\overset{\|}{C}}$—, —$SO_2$—OAlk(Ar), Alk(Ar)O—$\overset{S}{\overset{\|}{C}}$—, Alk(Ar)—S—$\overset{O}{\overset{\|}{C}}$—, Alk(Ar)S—$\overset{S}{\overset{\|}{C}}$—, Alk(Ar)$\overset{H}{N}$—$\overset{O}{\overset{\|}{C}}$—, (Alk,Ar)$_2$N—$\overset{O}{\overset{\|}{C}}$—, Alk(Ar)—$\overset{H}{N}$—$\overset{S}{\overset{\|}{C}}$—, (Alk,Ar)$_2$N—$\overset{S}{\overset{\|}{C}}$—, Alk(Ar)—$\overset{H}{N}$—$SO_2$—, (Alk,Ar)$_2$N—$SO_2$—, Alk(Ar)—N=N— and further, $R^1$ and $R^3$ together, or $R^2$ and $R^4$ together, denote =O, =S, =NH, =NAlk(Ar), =N—OH, =N—OAlk(Ar), =C(H,Alk,Ar)$_2$, =N—$\overset{H}{N}$—Alk(Ar)

or =N—N(H,Alk,Ar), and the radicals $R^8$ and $R^9$, $R^{11}$ and $R^{12}$, $R^{13}$ and $R^{14}$, $R^{15}$ and $R^{16}$, $R^{21}$ and $R^{22}$, and $R^{23}$ and $R^{24}$ may be linked via bridges with one or more carbon or hetero (O, N, S) atoms, have a good herbicidal and growth-regulating action which is better than that of prior art active ingredients.

The following route to compounds III to V, with R being $CH_3$— and $C_2H_5$—, has been disclosed: reaction of quadricyclane (I) with azodicarboxylic acid diesters (II) to give III, which is converted into IV by saponification and decarboxylation and, without isolation of IV, into the azo compound V by oxidation with $CuCl_2$, over a $Cu^I$ complex (JACS, 91, 5668, 1969).

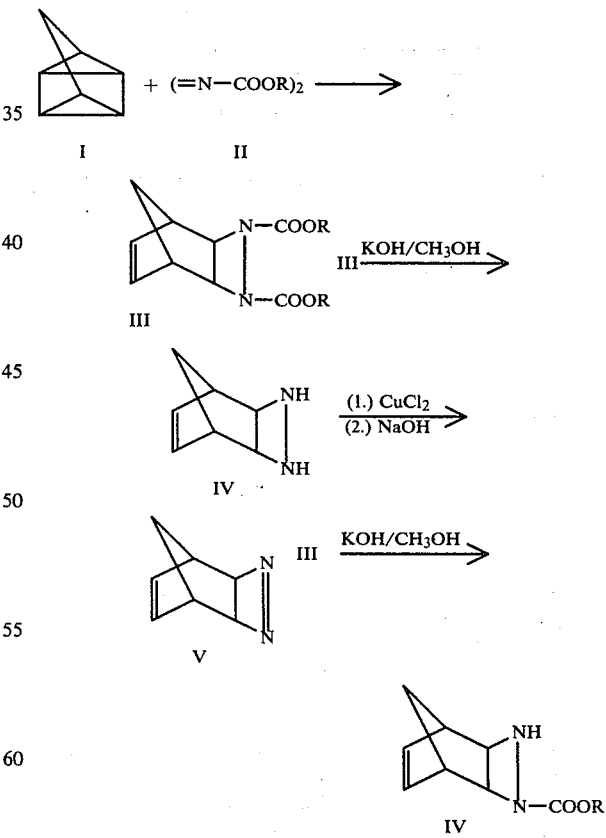

The compound VI is obtained by partial saponification and decarboxylation of III.

Furthermore, the compound VII is known (J. Org. Chem., 33, 370 1968).

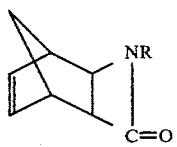

VII  R = H, —SO₂Cl

The active ingredients according to the invention may be prepared from these known compounds as follows.

(1) Manufacture of the compounds described in Examples 1 to 4 and the table pertaining thereto.

Reaction of compounds III to VII with 1,3-dipolar agents.

The frequently described (Houben-Weyl, 5/1b, 1119 et seq., and literature cited there) reaction of the unsubstituted norbornene with 1,3-dipolar agents to give polycyclic five-ring systems may also be carried out with the norbornene derivatives III to VII. The corresponding $\Delta^1$- or $\Delta^2$-pyrazoline, $\Delta^2$-triazoline, pyrazolidine, isoxazolidine and $\Delta^2$-isoxazoline derivatives of compounds III to VII may be prepared in this manner by addition of stable 1,3-dipolar agents, e.g., diazo compounds, azides, azomethinimines and azomethine oxides, or of 1,3-dipolar agents which are prepared in known manner in situ, e.g., nitrile oxides and nitrilimines.

In some cases, the corresponding cyclopropane or aziridine derivatives are formed under the reaction conditions from the $\Delta^1$-pyrazolines or triazolines primarily formed, by elimination of $N_2$.

With the stable triazolines and $\Delta^1$-pyrazolines, $N_2$ is eliminated by heating them in inert solvents at from 80° to 140° C., or, in the case of triazolines, by adding acids, e.g., trifluoroacetic acid, acetic acid or sulfuric acid, at from 20° to 80° C. (Examples 2D and 3B).

The reaction of the $\Delta^1$- or N-H-$\Delta^2$-pyrazoline compounds with carboxylic acids, carboxylic acid or thiocarboxylic acid halides, carboxylic acid anhydrides, esters of chlorocarbonic acid and thiochlorocarbonic acid, phosgene, sulfo acids, sulfonyl halides, sulfynyl halides, sulfenyl halides, alkyl, alkenyl or alkynyl halides, aldehydes or ketones, isocyanates, mustard oils, and carbamoyl or thiocarbamoyl halides gives, as a result of the elimination of water or hydrogen halide, or as a result of the addition of the N—H group on to the C=O or C=N double bond, the corresponding N-substituted $\Delta^2$-pyrazoline derivatives.

These reactions are carried out in accordance with well-known methods by heating the compounds, if desired in inert solvents and in the presence of auxiliary bases, e.g., tertiary amines, alkali metal carbonates or bicarbonates, sodium methylate, sodium hydride, alkali metal hydroxide, etc., at from 20° to 160° C. (Example 2B).

2. Manufacture of the compounds described in Example 5A and the table pertaining thereto.

Ring opening of the $\Delta^2$-triazoline or aziridine derivatives of III to VII with acids.

The $\Delta^2$-triazoline or aziridine derivatives of compounds III to VII may be converted into the corresponding 1,2-aminohalogen, 1,2-aminohydroxy or 1,2-aminoacyloxy derivatives with hydrogen halides in water or inert solvents, or with aqueous sulfuric acid or carboxylic acids. The reaction takes place readily by mixing the components in water or inert solvents at from −20° to +30° C., or by heating the reaction mixture at 40° to 130° C.

3. Manufacture of the compounds described in Examples 5B-E and the table pertaining thereto.

Reaction of compounds III to VII with halogens or halogen compounds, or nitric oxides or nitrogen-oxygen acids.

Numerous halogen or nitrogen compounds may be synthesized by reaction of the carbon double bond of the norbornene derivatives III to VII with halogens or halogen compounds, or nitric oxides or nitrogen-oxygen acids. The reactions have been extensively described in the literature with reference to acyclic and cyclic olefins (e.g., norbornene) (Houben-Weyl, 5/1b, 981 et seq., 5/3, 72, 95, 529, 762 and 813 et seq/., 5/4, 38 and 533 et seq., and 10/1, 61 et seq.,; Synthesis 1977, 462 et seq.), and may also be applied to derivatives III to VII. Thus, reaction with halogens, interhalogen compounds, hydrogen halides, hypohalides, halogen pseudohalides (azides, cyamides, cyanates, thiocyanates), halogen-nitrogen compounds (NOCl, NO₂Cl, NO₂I, N-halocarboxylic acid or -sulfonic acid amides or imides, etc.), halogen-sulfur compounds (sulfenyl halides, sulfonyl halides, etc.), nitric oxides (N₂O₃, N₂O₄, N₂O₅) or nitrogen-oxygen acids (e.g., HNO₃) gives the corresponding addition compounds (Examples 5B-D).

From some adducts of III or VII (R=SO₂Cl), the corresponding adducts of V or VII (R=H) may be prepared analogously to the conversion of III→V or VII (R=SO₂Cl)→VII (R=H), the monosubstituted norbornene derivatives also being formed to a certain extent as a result of hydrogen halide elimination (reverse formation of the carbon double bond).

The halogen, pseudohalogen, nitric oxide and hydroxy compounds listed under 2. and 3. may be converted into numerous products in accordance with methods known in the art.

Thus, for instance, the halogen compounds may be converted into the corresponding alkyl (aryl) ethers or thioethers, or hydroxy derivatives by substitution with alkali metal hydroxides, and alkali metal alcoholates, phenolates, thiolates or thiophenolates:

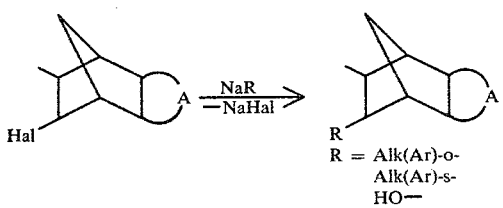

R = Alk(Ar)-o-
Alk(Ar)-s-
HO—

The nitric oxide derivatives (ON—, O₂N—) may be converted into the oxime compounds by isomerization, and into the keto derivatives, nitroolefin compounds or their derivatives by hydrolysis, e.g.,

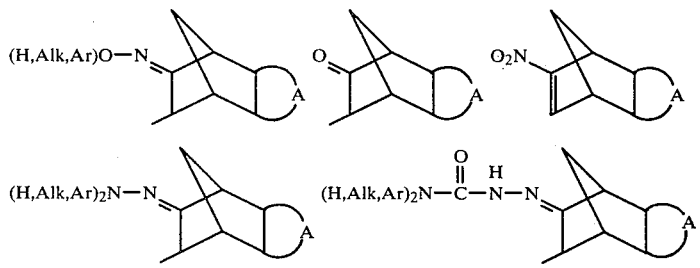

The hydroxy derivatives may be converted into the corresponding O-substituted derivatives by reaction with carboxylic acids, carboxylic or thiocarboxylic acid halides, chlorocarbonic or thiochlorocarbonic acid esters, phosphoric acid halides, phosphonic acid halides, thiophosphoric acid halides, thiophosphonic acid halides, phosgene, sulfonyl halides, sulfynyl halides, isocyanates, mustard oils, and carbamoyl or thiocarbamoyl halides by elimination of water or hydrogen halide, or by addition of the O—H group on to the C=O or C=N double bond:

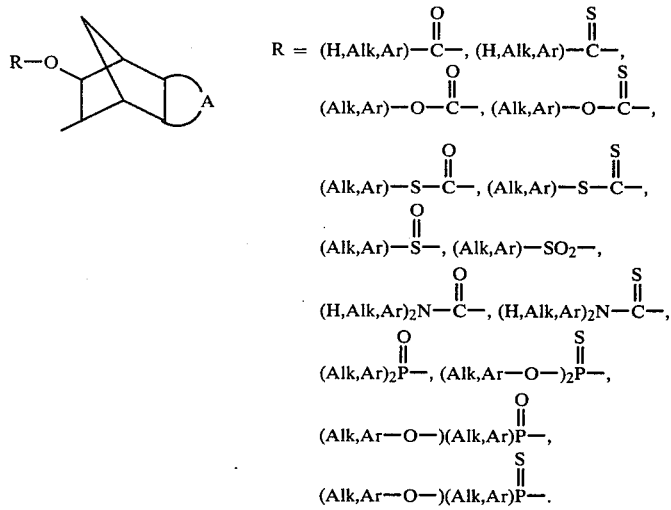

The mono- or di-nitric oxide compounds (ON—, $O_2N-$, =N—OH) may be converted by hydrogenation into the corresponding mono- and diamine compounds, which in turn may be further reacted analogously to the hydroxy derivatives, as described above.

4. Manufacture of the compounds described in Example 6 and the table pertaining thereto.

Oxidation of compounds III to VII, or derivatives prepared therefrom according to 1., 2., and 3.

The carbon double bond of the norbornene derivatives III to VII and/or the nitrogen double bond of the norbornene derivative V or the derivatives of V, which may be prepared by the methods described above (1., 2. and 3.), may be oxidized in known manner. Reaction with organic per-acids (Houben-Weyl, 6/3, 385 et seq., 10/2, 787 et seq.) gives the corresponding oxirane and/or azoxy derivatives, and reaction with $OsO_4$ or other oxidants (e.g., $KMnO_4$) gives the diol or hydroxyketone derivatives (Houben-Weyl, 4/1b, 604 et seq. and 861 et seq.).

If the compounds oxidized with per-acids contain thiolether groups, the sulfone or sulfoxy derivatives are formed.

The oxirane, sulfone or sulfoxy derivatives of V may be prepared from the corresponding derivatives of III in analogy to the conversion of III→V.

5. Manufacture of the compounds described in Example 7 and the table pertaining thereto.

Reaction of compounds III to VII with $S_4N_4$.

Compounds III to VII react with $S_4N_4$ in inert solvents at 80° to 130° C. to give the corresponding cyclic 5-membered trithiolane derivatives.

6. Manufacture of compound VI and the starting compounds described in Example 8 and the table pertaining thereto.

The reaction of compounds IV or VI with carboxylic or thiocarboxylic acid halides, carboxylic acid anhydrides, chlorocarbonic or thiochlorocarbonic acid ester, phosgene, sulfonyl halides, sulfynyl halides, alkyl, alkenyl, alkynyl or aralkyl halides, aldehydes or ketones, isocyanates, mustard oils, and carbamoyl or thiocarbamoyl halides gives the corresponding N-substituted or N,N'-disubstituted derivatives as a result of hydrogen halide elimination or addition of the N—H group on to the C=O or C=N double bond.

These reactions are carried out in accordance with the art, in inert solvents and usually in the presence of bases, e.g., tertiary amines, alkali metal carbonates or bicarbonates, sodium methylate, sodium hydride, alkali metal hydroxides, etc., at from 20° to 130° C.

Reaction of quadricyclane with alkyl-, aryl- or aralkylazodicarboxylic acid diesters gives the corresponding N,N'-disubstituted derivatives.

The compounds listed under 6. can be further reacted as described above under 1. to 5. (Examples 1, 2, 4, 5, 6 and 7).

The structure of the active ingredients was confirmed by nmr, infrared or mass spectroscopy, or by elemental analysis.

The melting and decomposition points given are uncorrected.

EXAMPLE 1

A.

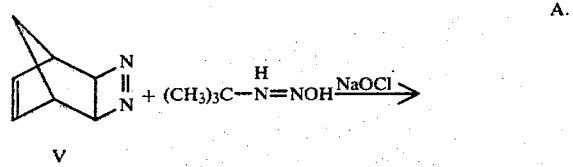

V

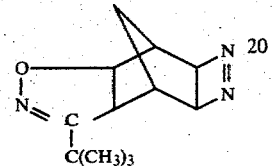

At 10° C., 25 parts (by weight) of aqueous NaOCl (about 13% free chlorine) is dripped into 10 parts of V and 8.3 parts of pivalylaldoxime in 100 parts of CH$_2$Cl$_2$. The organic phase is separated, dried with MgSO$_4$ and concentrated at 25° C. and 15 mm Hg. Yield: 14 parts (77% of theory). Melting point: 132° C. (decomposes) (ligroin).

B.

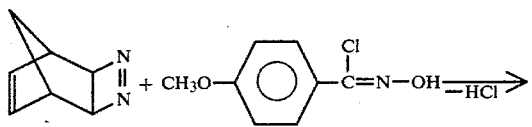

V

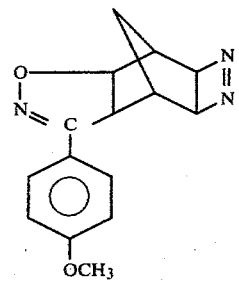

32 parts of p-methoxychlorobenzaldoxime is added to 20.6 parts of V, 196 parts of triethylamine and 400 parts of ether; the mixture is stirred for 12 hours at 25° C. The solid is filtered, washed with 100 parts of water and dried. Yield: 25.2 parts (55% of theory). Melting point: 160° C. (decomposes) (toluene/ligroin).

The folling compounds were prepared in accordance with Example 1:

| R | A | m.p. [°C.] | |
|---|---|---|---|
| CH$_3$— | —N=N— | 98 | |
| " | —N(H)—C(=O)— | 80 | * |
| " | —N(COOCH$_3$)—N(COOCH$_3$)— | 128 | |
| " | —N(S=C—N(H)—C$_6$H$_5$)—N(COOCH$_3$)— | | * |
| (CH$_3$)$_3$C— | —N(COOCH$_3$)—N(COOCH$_3$)— | 140 | |
| " | —N(H)—C(=O)— | 145 | * |
| ⟨H⟩ | —N=N— | 115 | |
| " | —N(COOCH$_3$)—N(COOCH$_3$)— | | |
| " | —N=N— | | |
| n-C$_{11}$H$_{23}$— | " | | |
| " | —N(H)—C(=O)— | | * |
| " | —N(COOCH$_3$)—N(COOCH$_3$)— | | |
| C$_6$H$_5$— | —N=N— | 173 | |
| p-Br—C$_6$H$_4$— | " | 196 | |

-continued

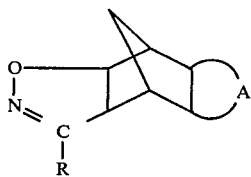

| R | A | m.p. [°C.] | |
|---|---|---|---|
| " | −N−N−<br>  \|   \|<br>  H   COOCH$_3$ | 141 | * |
| p-Cl−C$_6$H$_4$− | −N=N− | 185 | (decomposes) |
| " | −N−C−<br>  \|   \|\|<br>  H   O | 214 | * |
| " | −N————N−<br>  \|           \|<br>  COOCH$_2$C$_6$H$_5$ COOCH$_2$C$_6$H$_5$ | 60 | (decomposes) |
| " | −N————N−<br>CH$_2$  ⟩O⟨  COOCH$_3$<br>  \\N  (4-Cl-C$_6$H$_4$) | | * |
| p-CH$_3$−C$_6$H$_4$− | −N=N− | 181 | (decomposes) |
| p-NO$_2$−C$_6$H$_4$− | " | 212 | (decomposes) |
| " | −N−N−<br>  \|   \|<br>  H   COOCH$_3$ | 167 | * |
| " | −N————N−<br>  \|           \|<br>  COOCH$_3$ COOCH$_3$ | 169 | |
| (CH$_3$)$_2$N−C$_6$H$_4$− | −N=N− | 182 | (decomposes) |
| 2,4-Cl$_2$-6-CH$_3$-C$_6$H$_2$− | " | 161 | |
| " | −N−C−<br>  \|   \|\|<br>  H   O | 205 | (decomposes) |
| 3,5-Cl$_2$-2-OH-C$_6$H$_2$(CH$_3$)− | " | 93 | * |
| 1-CH$_3$-naphthyl | −N=N− | 80 | |
| " | −N————N−<br>  \|           \|<br>  SO$_2$C$_6$H$_5$ COOCH$_3$ | 185 | (decomposes) |
| 1-CH$_3$-anthryl | −N=N− | 110 | (decomposes) |
| 2-CH$_3$-furyl | " | | |
| " | −N————N−<br>  \|           \|<br>  COOCH$_3$ COOCH$_3$ | 120 | |
| " | −N————N−<br>  \|\|           \|<br>O=C−SCH$_2$C$_6$H$_5$ COOCH$_3$ | | * |
| 3-CH$_3$-thienyl | −N————N−<br>  \|           \|<br>  COOCH$_3$ COOCH$_3$ | 160 | |
| " | −N=N− | 148 | (decomposes) |

-continued

| R | A | m.p. [°C.] |
|---|---|---|
| " | —NH—C(=O)— | 150 |
| " | —N(O=C-NH-CH₃)—N(COOCH₃)— | * |
| (4-pyridyl) | —N=N— | 125 |
| " | —NH—C(=O)— | * |
| (indol-3-yl) | —N=N— | |
| " | —N(COOCH₃)—N(COOCH₃)— | |
| (oxazoline-norbornane-azo structure) | —N=N— | 216 (decomposes) |
| (oxazoline-norbornane-amide structure) | —NH—C(=O)— | * |

* position isomers

EXAMPLE 2

A. 3.6 parts of V and 6 parts of diphenyldiazomethane are stirred for 6 hours in 35 parts of toluene at 80° C. After cooling, the solid is filtered and washed with 50 parts of petroleum ether. Yield: 5.8 parts (61% of theory). Melting point: 203° C. (decomposes) (toluene/ligroin).

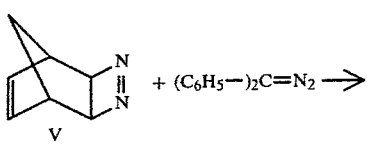

V + (C₆H₅—)₂C=N₂ →

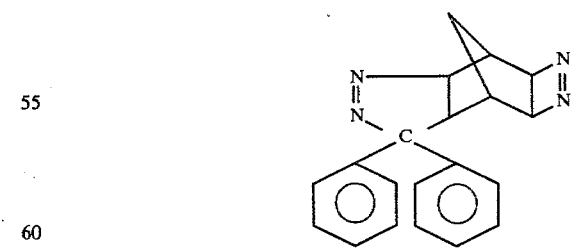

B.

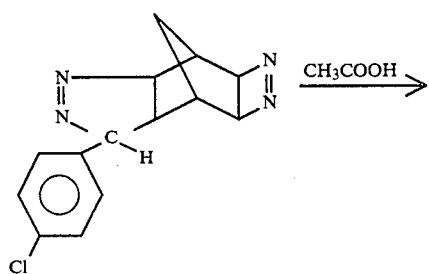

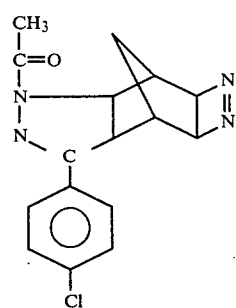

5 parts of the p-chlorophenyl-Δ¹-pyrazoline derivative of V is stirred in 100 parts of acetic acid for 4 hours at 60° C. After the solution has cooled, it is treated with 0.5 part of activated carbon and, after filtration, concentrated at 50° C. and 15 mm Hg. The residue is washed with 50 parts of petroleum ether. Yield: 4.2 parts (75% of theory). Melting point: 197° C. (decomposes).

C.

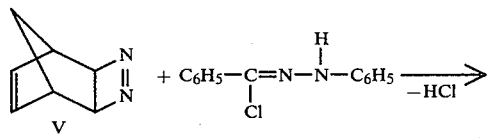

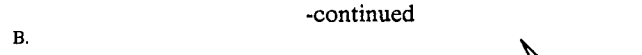

13 parts of V and 23 parts of benzophenyl hydrazide chloride are heated in 100 parts of toluene at 80° C., and 40 parts of triethylamine is slowly added. After 3 hours, the reaction mixture is cooled to 25° C. and filtered. The residue is washed with 100 parts of water and dried. Yield: 17 parts (55% of theory). Melting point: 178° C. (decomposes) (toluene/ligroin).

D.

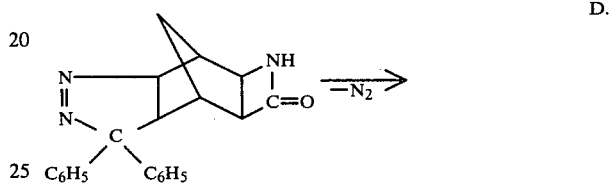

5 parts of the diphenylpyrazoline derivative is heated in 100 parts of xylene for 15 hours at 140° C. The solvent is then distilled off at 40° C. and 20 mbars, and the residue is washed with 50 parts of petroleum ether. Yield: 4.1 parts (90% of theory). Melting point: 181° C. (toluene/ligroin).

The following compounds were prepared similarly to Examples 2A to C:

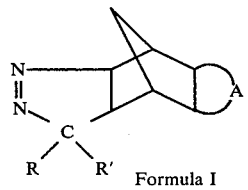 Formula I

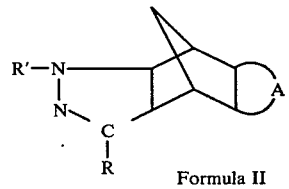 Formula II

| Formula | R' | R | A | m.p. [°C.] | |
|---------|------|-----------|----------------------------------|-----|---------------|
| I | H— | H— | —N=N— | 112 | (decomposes) |
| " | " | " | —N——N—<br>      \|     \|<br>    COOCH₃ COOCH₃ | 156 | (decomposes) |
| " | CH₃— | " |       O<br>  H  \|\|<br>—N—C— | | * |
| " | " | " | —N=N— | | |
| II | H— | C₂H₅OCO | " | 134 | (decomposes) |
| " | " | " |       O<br>  H  \|\|<br>—N—C— | 82 | * |
| " | " | " | —N——N—<br>      \|     \|<br>    COOCH₃ COOCH₃ | 135 | (decomposes) |

-continued

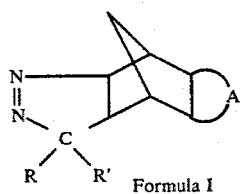
Formula I

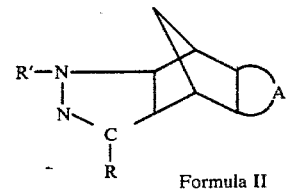
Formula II

| Formula | R' | R | A | m.p. [°C.] |
|---|---|---|---|---|
| " | " | " | $-N-N-$<br>$\phantom{-N-}|\phantom{-}\phantom{-}COOC_6H_5$<br>$COOC_6H_5$ | 143 (decomposes) |
| " | " | $CH_3-\overset{\overset{O}{\|}}{C}-$ | $-N=N-$ | 137 (decomposes) |
| " | $C_2H_5OCO$ | " | " | 135 (decomposes) |
| " | " | " | $-N-N-$<br>$\phantom{-N-}|\phantom{-}\phantom{-}COOCH_3$<br>$COOCH_3$ | 192 |
| I | $CH_3-$ | " | $-N=N-$ | * |
| " | $CH_2=CH-CH_2-$ | $C_2H_5OCO-$ | $-\overset{H}{N}-\overset{\overset{O}{\|}}{C}-$ | |
| " | $C_6H_5-CH_2-$ | " | $-N-N-$<br>$\phantom{-N-}|\phantom{-}\phantom{-}COOCH_2C_6H_5$<br>$COOCH_2C_6H_5$ | * |
| " | $C_6H_5-$ | $H-$ | $-N=N-$ | 172 (decomposes) |
| " | " | $C_6H_5-$ | $-\overset{H}{N}-\overset{\overset{O}{\|}}{C}-$ | 217 * |
| II | " | $CH_3-$ | $-N=N-$ | (decomposes) |
| " | $p\text{-}Cl-C_6H_4$ | $HCO-$ | " | 148 (decomposes) |
| " | " | " | $-N-N-$<br>$\phantom{-N-}|\phantom{-}\phantom{-}COOCH_3$<br>$COOCH_3$ | |
| I | $C_6H_5-$ | $C_6H_5-$ | " | 130 (decomposes) |
| II | " | " | $-\overset{H}{N}-\overset{\overset{O}{\|}}{C}-$ | 185 (decomposes) |
| " | " | " | $-N-N-$<br>$\phantom{-N-}|\phantom{-}\phantom{-}COOCH_3$<br>$COOCH_3$ | 182 (decomposes) |
| " | $CH_3-$ | " | $-N=N-$ | |
| " | $C_6H_5-\overset{\overset{O}{\|}}{C}-$ | $O_2N-\underset{NO_2}{\underset{|}{\bigcirc}}$ | $-\overset{H}{N}-\overset{\overset{O}{\|}}{C}-$ | * |
| I | $p\text{-}Cl-C_6H_4-$ | $H-$ | $-N=N-$ | 149 (decomposes) |
| " | " | " | $-N-N-$<br>$\phantom{-N-}|\phantom{-}\phantom{-}\overset{H}{\phantom{|}}$<br>$COOCH_3$ | 90 * |
| II | " | $CH_3-\overset{H}{N}-\overset{\overset{O}{\|}}{C}-$ | $-N-N-$<br>$\phantom{-N-}|\phantom{-}\phantom{-}COOCH_3$<br>$COOCH_3$ | |
| " | " | " | $-N=N-$ | |
| " | " | $CH_3-\overset{H}{N}-\overset{\overset{S}{\|}}{C}-$ | " | |
| " | " | " | $-N-N-$<br>$\phantom{-N-}|\phantom{-}\phantom{-}COOCH_3$<br>$COOCH_3$ | |
| " | " | $C_6H_5-\overset{H}{N}-\overset{\overset{O}{\|}}{C}-$ | " | |
| " | " | " | $-N=N-$ | |
| " | " | $C_6H_5-\overset{H}{N}-\overset{\overset{S}{\|}}{C}-$ | $-N-N-$<br>$\phantom{-N-}|\phantom{-}\phantom{-}COOCH_3$<br>$COOCH_3$ | |

-continued

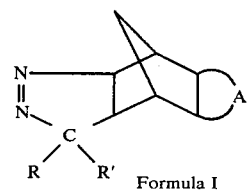
Formula I

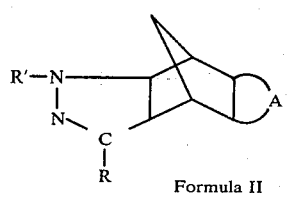
Formula II

| Formula | R' | R | A | m.p. [°C.] | |
|---|---|---|---|---|---|
| " | " | " | —N=N— | | |
| " | " | C₆H₅— | " | | |
| " | " | (CH₃)₂CH—C(=O)— | " | | |
| " | " | " | —N—N—(COOCH₃)(COOCH₃) | | |
| I | p-CH₃—C₆H₄— | H— | —N—N—(COOCH₃)(H) | 91 | * |
| " | " | " | —N(H)—C(=O)— | 230 | (decomposes) |
| " | p-Cl—C₆H₄ | " | —N—N—(COOCH₃)(COOCH₃) | 156 | (decomposes) |
| " | m-NO₂—C₆H₄— | " | —N=N— | | |
| " | (methylenedioxyphenyl-CH₂—O) | " | —N(H)—C(=O)— | | * |
| " | (1-naphthyl) | " | —N=N— | | |
| " | " | R + R' = (9,9-fluorenyl) | —N—N—(COOCH₃)(COOCH₃) | 98 | |
| " | " | H— | —N=N— | | |
| " | (3-methylthienyl) | " | —N(H)—C(=O)— | | * |
| II | C₂H₅OCO | C₆H₅SO₂— | —N—N—(COOCH₃)(COOCH₃) | | |
| " | p-Cl—C₆H₄— | (2-nitrobenzoyl) | —N=N— | | |
| " | C₂H₅OCO— | (nicotinoyl) | —N—N—(COOCH₃)(COOCH₃) | | |
| " | C₆H₅— | C₆H₅— | —N—N—(COOCH₃)(S=C—N(H)—C₆H₅) | | * |
| " | p-Cl—C₆H₄— | p-Cl—C₆H₄— | —N=N— | | |
| " | C₂H₅OCO— | (CH₃)₃—(4-tert-butylcyclohexyl)—OC(=O)— | —N=N— | | |

-continued

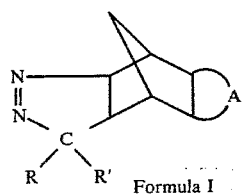 Formula I

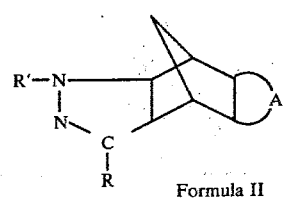 Formula II

| Formula | R' | R | A | m.p. [°C.] |
|---|---|---|---|---|
|  | 3-pyridyl | C₆H₅— | " |  |
| " | " | " | —NH—C(=O)— | * |
| " | " | " | —N=N— |  |
| " | 2-thienyl | " |  |  |
| " | " | " | —N(COOCH₃)—N(COOCH₃)— |  |
| " | indol-3-ylmethyl | p-Cl—C₆H₄— | —N=N— |  |
| " | " | " | —NH—C(=O)— | * |
| I | 2-furyl | H— | —N=N— |  |
| " | " | " | —N(COOCH₃)—N(COOCH₃)— |  |
| " | indol-3-yl | " | " |  |
| " | " | " | —N=N— |  |
| II | 1-methyl-4-nitroimidazol-2-yl | C₆H₅— | " |  |
| " | " | " | —N(COOCH₃)—N(COOCH₃)— |  |
| " | " | CH₃— | " |  |
| " | " | " | —N=N— |  |
| " | " | " | —NH—C(=O)— | * |

*position isomers

The following compounds were prepared in accordance with Examples 2A and D:

| R | R' | A | m.p. [°C.] |
|---|---|---|---|
| R + R' = (fluorene) | | $-N=N-$ | 186 (decomposes) |
| " | | $-N(H)-C(=O)-$ | 270 |
| " | | $-N(COOCH_3)-N(H)-$ | 166 |
| " | | $-N(COOCH_3)-N(COOCH_3)-$ | 243 |
| " | | $-N(COOC_6H_5)-N(COOC_6H_5)-$ | 92 |
| " | | $-N(CONCH_3)-N(COOCH_3)-$ | |
| " | | $-N(SO_2C_6H_5)-N(COOCH_3)-$ | |
| " | | $-N(OC-SCH_2C_6H_5)-N(COOCH_3)-$ | |
| $C_6H_5-$ | $C_6H_5-$ | $-N=N-$ | |
| $C_6H_5-$ | $C_6H_5$ | $-N(COOCH_3)-N(COOCH_3)-$ | |
| $CH_2=CH-CH_2-$ | $C_2H_5O-C(=O)-$ | $-N(H)-C(=O)-$ | |
| $C_6H_5-CH_2-$ | $C_2H_5O-C(=O)-$ | $-N=N-$ | |
| $CH_3-$ | $CH_3-C(=O)-$ | $-N(COOCH_3)-N(COOCH_3)-$ | |
| $CH_3-$ | $CH_3-$ | $-N(COOCH_3)-N(COOCH_3)-$ | |
| " | " | $-N=N-$ | |
| $CH_3-$ | $CH_3-$ | $-N(H)-C(=O)-$ | |
| $C_6H_5-$ | " | " | |
| " | " | $-N=N-$ | |
| " | " | $-N(COOCH_3)-N(COOCH_3)-$ | |
| R + R' = (fluorene) | | $-N(CH_2-C(=N-O-N=C(-C_6H_4-Cl)))-N(COOCH_3)-$ | |
| " | | $-N(OC-(CH_2)_7-CH=CH-(CH_2)_7-CH_3)-N(H H COOCH_3)-$ | |

EXAMPLE 3

5 parts of VII and 3.4 parts of p-bromophenyl azide are stirred for 6 hours in 40 parts of toluene at 80° C. After cooling, the Δ¹-1,2,3-triazoline derivative which has formed (position isomers) is filtered and washed with 50 parts of petroleum ether. Yield: 7.4 parts (88% of theory). Melting point: 208° C. (decomposes).

6.8 parts of the above Δ¹-1,2,3-triazoline derivative (isomer mixture) is stirred for 4 hours in 25 parts of acetic acid and 25 parts of ether at 25° C. The aziridine derivative is filtered and washed with 20 parts of ether. Yield: 6.1 parts (90% of theory). Melting point: 228° C.

The following compounds were prepared in accordance with Example 3:

| Formula | Formula I R | Formula II m.p. [°C.] |
|---|---|---|
| II | $CH_3-SO_2-$ | 101 * |
| I | $C_3H_7-$ | 105 (decomposes) |
| II | $C_4F_9-SO_2-$ | 172 (decomposes) |
| I | $C_{12}H_{25}-$ | 126 * |
| " | cyclohexyl-H- | * (decomposes) |
| " | piperidino-$CH_2-CH_2-$ | * |
| " | $C_6H_5-CH_2-$ | 185 * |
| " | $O_2N-C(=CH)-N(CH_3)-N=C(CH_2-)$ | 196 * (decomposes) |
| " | (Cl-C_6H_4)-C(=N-O-N=C)-CH_2- | * |
| " | $p-Cl-C_6H_4-CH_2-$ | 120 * (decomposes) |
| " | $C_6H_5-$ | 200 * (decomposes) |
| II | " | 237 (decomposes) |
| " | $C_6H_5-SO_2-$ | 214 |
| " | $p-Cl-C_6H_4-SO_2-$ | 185 * (decomposes) |
| I | $p-F-C_6H_4-$ | 230 * (decomposes) |
| " | $C_6H_5-N=N-C_6H_4-$ | 236 * |
| " | " | 174 (decomposes) |
| I | $m-CF_3-C_6H_4-$ | |
| " | $H_3C-C_6H_3(NO_2)-$ | 216 * (decomposes) |
| " | Cl-C_6H_3-Cl (3,5-dichlorophenyl) | * |
| " | $OCF_2CHF_2$-phenyl- | |
| II | $O_2N-C_6H_3-SO_2CH_3$ | * |
| I | $HOOC-C_6H_4-$ | 199 * (decomposes) |
| " | benzothiazol-yl- | 242 |
| II | benzothiazol-yl- | 195 * |
| I | Cl-C_6H_3-NO_2 | |

-continued

| Formula | R | Formula I / Formula II m.p. [°C] |
|---|---|---|
| II | (CH₃)₂N—C₆H₄— | * |
| I | 3-Cl, 4-SO₃H-C₆H₃— | 115 (decomposes) |
| II | 2,4,5-trichloro-methylphenyl | * |
| I | benzodithiol-3-one | * |
| " | 2,6-dichloro-4-nitrophenyl | 141 (decomposes) |
| " | thiazol-2-yl | 153 (decomposes) |
| II | thiazol-2-yl | 176 |
| I | 1H-indazol-3-yl | * |
| I | 2,5-diethoxy-4-benzamidophenyl | 149 (decomposes) |
| II | " | * |
| I | (bicyclic triazoline with p-tolyl) | 185 (decomposes) |
| II | (bicyclic with p-tolyl N) | 326 (decomposes) |
| I | 1-naphthyl | * |

* position isomers

EXAMPLE 4

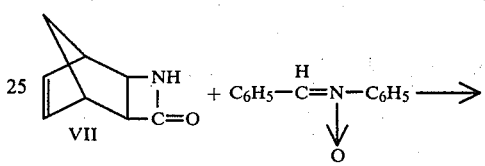

A.

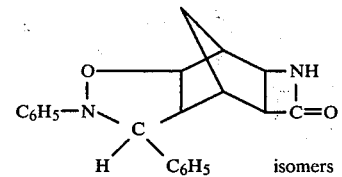

isomers 13.5 parts of VII and 19 parts of C,N-phenylnitrone are heated in 150 parts of toluene for 36 hours at 110° C. The mixture is then cooled to 25° C., extracted twice with 50 parts of water, dried with MgSO₄ and concentrated at 40° C. and 20 mbars. The residue is washed with 50 parts of a 1:2 mixture of ether and petroleum ether. Yield: 2.3 parts (71% of theory). Melting point: 194° C. (toluene/ligroin).

B.

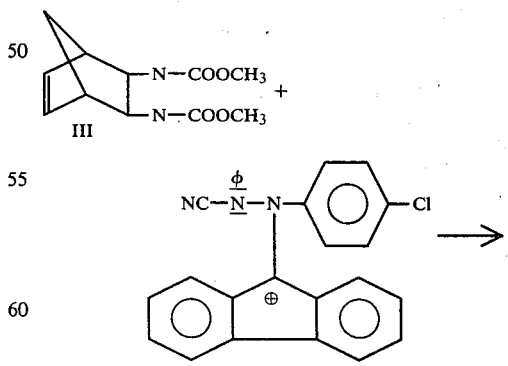

-continued

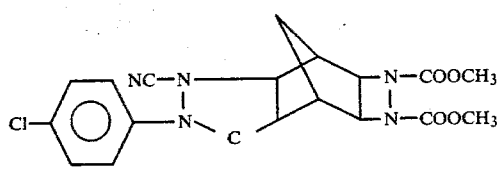

2.1 parts of III and 3 parts of the azomethinimine derivative are heated in 40 parts of toluene for 72 hours at 100° C. After the toluene has been distilled off at 30° C. and 15 mbars, the residue is washed with 50 parts of a 1:2 mixture of ether and petroleum ether. Yield: 3.6 parts (70% of theory). Melting point: 155° C.

The following compounds were prepared in accordance with Example 4:

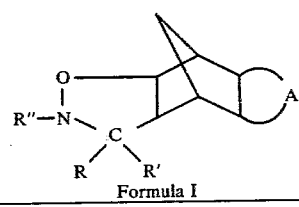
Formula I

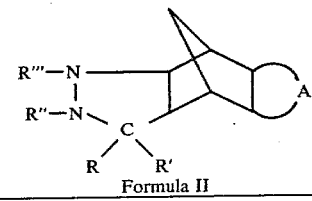
Formula II

| Formula | R | R' | R'' | R''' | A | m.p. [°C.] |
|---|---|---|---|---|---|---|
| I | C$_6$H$_5$— | H— | C$_6$H$_5$— | — | —N—N— <br> \| \| <br> COOCH$_3$ COOCH$_3$ | 98 * |
| " | " | " | " | — | —N=N— | 76 * |
| " | p-Cl—C$_6$H$_4$— | " | " | — | O <br> H \|\| <br> —N—C— | 230 * |
| " | " | " | " | — | —N—N— <br> \| \| <br> COOCH$_3$ COOCH$_3$ | 89 * |
| " | " | " | " | — | —N=N— | 195 * (decomposes) |
| II | C$_6$H$_5$— | C$_6$H$_5$— | " | NC— | " | * |
| " | " | " | " | " | O <br> H \|\| <br> —N—C— | * |
| " | " | " | " | " | —N—N— <br> \| \| <br> COOCH$_3$ COOCH$_3$ | * |
| I | CH$_3$— | H— | p-Cl—C$_6$H$_5$— | — | —N=N— | * |
| " | " | " | ⟨H⟩— | — | " | * |
| " | " | " | " | — | O <br> H \|\| <br> —N—C— | * |
| " | n-C$_3$H$_7$— | " | " | — | —N—N— <br> \| \| <br> COOCH$_3$ COOCH$_3$ | * |
| " | " | " | " | — | —N=N— | * |
| " | C$_6$H$_5$— | " | CH$_3$— | — | —N=N— | * |
| " | " | " | C$_6$H$_5$— | — | —N—N— <br> \| \| <br> COOC$_6$H$_5$ COOC$_6$H$_5$ | * |
| " |  | " | " | — | —N=N— | * |
| I | C$_6$H$_5$— | H— | C$_6$H$_5$— | — | —N————————N— <br> \| \| <br> O=CSCH$_2$—C=CCl$_2$ COOCH$_3$ <br> \| <br> Cl | * |
| " | " | " | " | — | —N=N— | * |
| " | Cl—⟨⟩— <br> \| <br> Cl | " | " | — | O <br> H \|\| <br> —N—C— | * |
| " | H$_3$C—⟨⟩— | " | " | — | —N=N— | * |
| " | Br—⟨⟩— | " | " | — | —N=N— | * |

-continued

| | 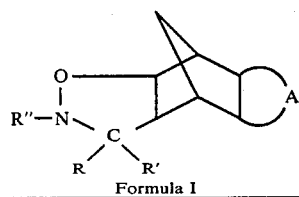 Formula I | | | | 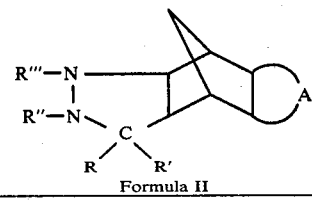 Formula II | |
|---|---|---|---|---|---|---|
| Formula | R | R' | R'' | R''' | A | m.p. [°C.] |
| " | (CH$_3$)$_2$N−⟨C$_6$H$_4$⟩− | " | " | − | −N(H)−C(=O)− | * |
| " | " | " | " | − | −N=N− | * |
| " | " | " | " | − | −N(COOCH$_3$)−N(COOCH$_3$)− | * |
| " | ⟨C$_6$H$_{11}$⟩− | " | " | − | " | * |
| " | " | " | " | − | −N=N− | * |
| " | O$_2$N−⟨C$_6$H$_4$⟩− | " | CH$_3$− | − | −N=N− | * |
| " | anthryl | " | C$_6$H$_5$− | − | " | * |
| " | " | " | " | − | −N(H)−C(=O)− | * |
| " | " | " | " | − | −N(COOCH$_3$)−N(COOCH$_3$)− | * |
| " | methylenedioxyphenyl | " | " | − | −N(COOCH$_3$)−N(COOCH$_3$)− | * |
| " | " | " | " | − | −N=N− | * |
| II | R + R' = 9,9-fluorenyl | p-Cl−C$_6$H$_4$− | NC− | − | −N(COOCH$_3$)−N(COOCH$_3$)− | 155 |
| " | " | " | " | " | −N(H)−C(=O)− | 204 * |
| " | " | " | " | " | −N=N− | * |
| I | C$_6$H$_5$− | " | C$_6$H$_5$− | − | −N−N(COOCH$_3$)−CH$_2$−C(=N−O−)−⟨C$_6$H$_4$Cl⟩ | * |
| II | H− | R' + R'' = CH$_2$−CH$_2$−⟨C$_6$H$_4$⟩ | | p-NO$_2$−C$_6$H$_4$− | −N(COOCH$_3$)−N(COOCH$_3$)− | * |
| " | " | " | " | " | −N(H)−C(=O)− | * |
| I | " | R' + R'' = CH$_2$−CH$_2$−C(CH$_3$)$_2$−CH$_2$ | | − | " | * |
| " | " | " | " | − | −N=N− | * |
| " | " | " | " | − | −N(COOCH$_3$)−N(COOCH$_3$)− | * |
| " | " | " | " | − | −N(SO$_2$C$_6$H$_5$)−N(COOCH$_3$)− | * |

-continued

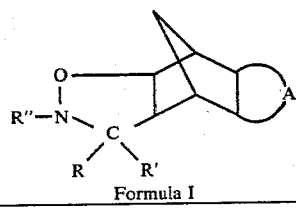
Formula I

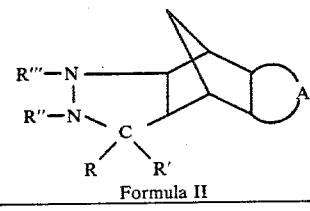
Formula II

| Formula | R | R' | R'' | R''' | A | m.p. [°C.] |
|---|---|---|---|---|---|---|
| " | " | " | " | — | −N(−C(=O)−NCH₃−H)−N−COOCH₃ | * |
| " | " | R' + R'' = −CH₂−CH₂−C₆H₄− | | — | −N−C(=O)H | * |
| " | " | " | " | — | −N(COOCH₃)−N(COOCH₃)− | * |
| " | " | " | " | — | −N=N− | * |
| " | (C₆H₅, oxazolidine-N=N bicyclic) | H− | C₆H₅− | — | −N=N− | * |
| " | (C₆H₅, oxazolidine-N−C(=O)H bicyclic) | " | " | — | −N−C(=O)H | * |
| " | (C₆H₅, oxazolidine-N(COOCH₃)−N(COOCH₃) bicyclic) | " | " | — | −N(COOCH₃)−N(COOCH₃)− | * |
| I | (thienyl) | H− | C₆H₅− | — | −N(COOCH₃)−N(COOCH₃)− | 193 * |
| " | " | " | " | — | −N−C(=O)H | * |
| " | " | " | " | — | −N=N− | 103 * |
| " | (furyl) | " | " | — | " | * |
| " | " | " | CH₃− | — | −N(COOCH₃)−N(COOCH₃)− | * |
| " | " | " | " | — | −N=N− | * |
| " | (indolyl) | " | C₆H₅− | — | " | * |
| " | " | " | " | — | −N−C(=O)H | * |
| " | " | " | " | — | −N(COOCH₃)−N(COOCH₃)− | * |

-continued

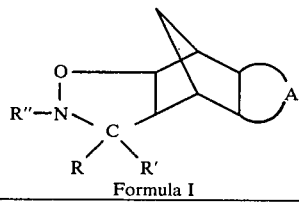
Formula I

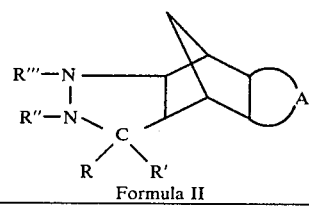
Formula II

| Formula | R | R' | R'' | R''' | A | m.p. [°C.] |
|---|---|---|---|---|---|---|
| " | $O_2N{-}C{=}N{-}CH{=}N{-}CH_3$ (imidazoline-like) | " | " | — | " | * |
| " | " | " | " | — | —N=N— | * |
| " | " | " | " | — | —N(H)—C(=O)— —N=N— | * |
| " | " | " | C6H11 (cyclohexyl) | — | —N=N— | * |
| " | " | " | " | — | —N(COOCH3)—N(COOCH3)— | * |

* isomers

EXAMPLE 5

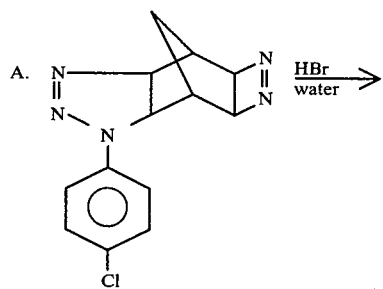

A. + HBr/water →

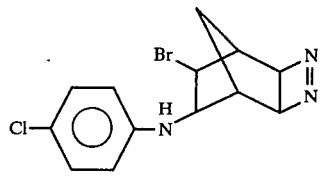
+ N₂

5.4 parts of the N-p-chlorophenyl-1-1,2,3-triazoline derivative is heated in 7 parts of 47% strength aqueous HBr and 50 parts of water for 5 hours at 100° C. After cooling, the solid is filtered and washed with 200 parts of water. Yield: 5.7 parts (88.5% of theory). Melting point: 185° C. (decomposes).

B. 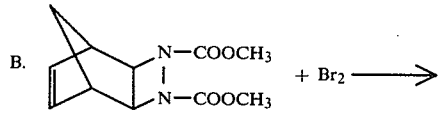 + Br₂ →

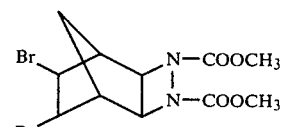

III

At −10° C., 10.1 parts of bromine in 25 parts of CH₂Cl₂ is dripped into 15 parts of III and 50 parts of CH₂Cl₂. The solution is stirred for 1 hour at −10° C., then treated with 0.5 part of activated carbon and filtered, and the filtrate is concentrated at 25° C. and 15 mm Hg. The residue is washed with 40 parts of petroleum ether. Yield: 20 parts (80% of theory). Melting point: 103° C.

C. 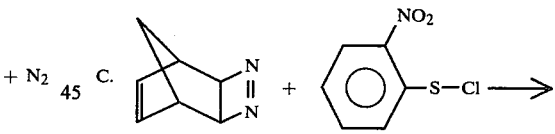 →

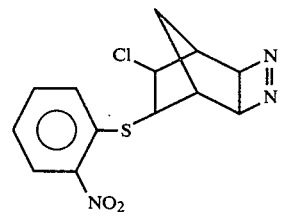

V 3.2 parts of V and 2 parts of 2-nitrophenylsulfenyl chloride are heated for 4 hours in 120 parts of CCl₄ at 76° C. After cooling, the precipitated solid is filtered and washed with 50 parts of petroleum ether. Yield: 4.0 parts 77% of theory). Melting point: 168° C. (decomposes) (toluene/ligroin).

D. 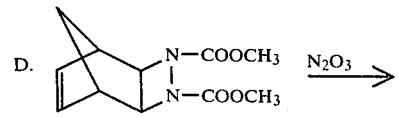 N₂O₃ →

III

-continued

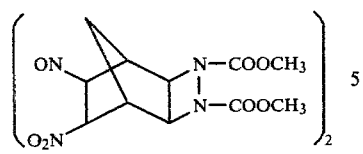

10 parts of III is dissolved in 100 parts of ether and 50 parts of dichloromethane, and NO and air (40-80 ml/min) are passed in, while stirring, for 1 hour at 0° to 15° C. The precipitate is filtered and washed with 100 parts of ether. Yield: 9.5 parts (72% of theory). Melting point: 120° C. (decomposes).

E.

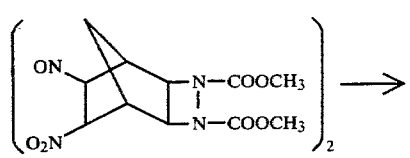

-continued

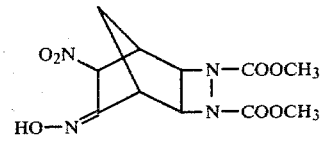

10 parts of the dimeric nitroso compound is heated in 25 parts of dimethylformamide for 30 minutes at 130° C., and the mixture is then poured into 200 parts of water. The water is extracted twice with 100 parts of dichloromethane. The organic phase is dried with MgSO$_4$ and concentrated at 30° C. and 20 mbars. Yield: 8 parts (80% of theory) of a yellow oil.

The following compounds were prepared in a manner similar to that described in Example 5:

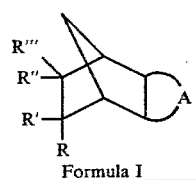  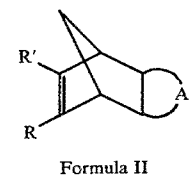

Formula I                                       Formula II

| Formula | R   | R'  | R'' | R''' | A                                                    | m.p. [°C.]      |
|---------|-----|-----|-----|------|------------------------------------------------------|-----------------|
| I       | Cl— | H—  | Cl— | H—   | —N=N—                                                | 93              |
| "       | "   | "   | "   | "    | —N—C— (H, O)                                         | 55*             |
| "       | "   | "   | "   | "    | —N———N— / COOCH$_3$  COOCH$_3$                       | 45              |
| "       | Br— | "   | Br— | "    | —N———N— / COOC$_2$H$_5$  COOC$_2$H$_5$               | 16              |
| "       | "   | "   | "   | "    | —N=N—                                                | 83              |
| "       | "   | "   | HO— | "    | —N———N— / COOCH$_3$  COOCH$_3$                       |                 |
| "       | "   | "   | "   | "    | —N=N—                                                |                 |
| "       | "   | "   | "   | "    | —N———————N— / OCOCH$_2$C$_6$H$_5$  OCOCH$_2$C$_6$H$_5$ |                 |
| "       | H—  | "   | H—  | Br—  | —N———N— / COOCH$_3$  COOCH$_3$                       |                 |
| "       | "   | "   | "   | "    | —N=N—                                                |                 |
| "       | "   | "   | "   | Cl—  | "                                                    |                 |
| "       | "   | "   | "   | I—   | "                                                    |                 |
| "       | "   | "   | "   | Cl—  | —N———N— / COOCH$_3$  COOCH$_3$                       |                 |
| "       | "   | "   | "   | I—   | "                                                    |                 |
| II      | Br— | "   | —   | —    | —N=N—                                                | b.p. (0.5 mm) 57 |
| "       | Cl— | "   | —   | —    | "                                                    | b.p. (3 mm) 55  |
| I       | F—  | "   | H—  | H—   | —N———N— / COOCH$_3$  COOCH$_3$                       |                 |
| "       | "   | "   | "   | "    | —N=N—                                                |                 |
| "       | Br— | "   | "   | "    | —N———N— / O=C—NCH$_3$ (H)  COOCH$_3$                 | *               |
| "       | "   | "   | "   | "    | —N———N— / SO$_2$C$_6$H$_5$  COOCH$_3$                | *               |

-continued

|  | 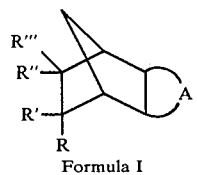 Formula I | | | | 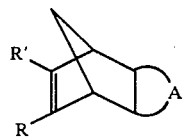 Formula II | |
|---|---|---|---|---|---|---|
| Formula | R | R' | R'' | R''' | A | m.p. [°C] |
| " | " | " | " | " | $-N\underset{O=COCH(CH_3)_2}{\underset{|}{-}}N\underset{O=COCH(CH_3)_2}{\underset{|}{-}}$ | |
| " | ON— | " | $O_2N$— | " | —N=N— | 95 (decomposes) |
| " | " | " | " | " | $-N\underset{OCOC_6H_5}{\underset{|}{-}}N\underset{OCOC_6H_5}{\underset{|}{-}}$ | |
| " | Cl— | " | Cl— | " | $-N\underset{SO_2Cl}{\underset{|}{-}}\underset{O}{\overset{\|}{C}}-$ | 35* |
| " | Br— | " | Br— | " | $\underset{H}{-N}-\overset{O}{\overset{\|}{C}}-$ | 141* |
| " | ON— | " | $O_2N$— | " | " | 116 * (decomposes) |
| " | Br— | " | Br— | " | $-N\underset{SO_2Cl}{\underset{|}{-}}\overset{O}{\overset{\|}{C}}-$ | 5* |
| " | Cl— | " | Cl— | " | $-N\underset{COOCH_3}{\underset{|}{-}}N\underset{\underset{H}{CON}-\text{(2,4-diClC}_6\text{H}_3\text{)}}{\underset{|}{-}}$ | 85* |
| " | Br— | " | Br— | " | $-N\underset{CH_2}{\underset{|}{-}}N\underset{COOCH_3}{\underset{|}{-}}$ fused with isoxazoline-(4-ClC_6H_4) | * |
| " | $CFCl_2$—S— | " | Cl— | " | $-N\underset{COOCH_3}{\underset{|}{-}}N\underset{COOCH_3}{\underset{|}{-}}$ | |
| " | " | " | " | " | —N=N— | |
| " | Br— | " | Br— | " | $-N\underset{COOC_6H_5}{\underset{|}{-}}N\underset{COOC_6H_5}{\underset{|}{-}}$ | 91 |
| " | " | " | " | " | $-N\underset{\underset{H}{OCNC_6H_5}}{\underset{|}{-}}N\underset{COOCH_3}{\underset{|}{-}}$ | 127* |
| " | Cl— | " | $CF_3$—S— | " | —N=N— | |
| " | " | " | " | " | $\underset{H}{-N}-\overset{O}{\overset{\|}{C}}-$ | * |
| " | " | " | " | " | $-N\underset{COOCH_3}{\underset{|}{-}}N\underset{COOCH_3}{\underset{|}{-}}$ | 79 |
| " | " | " | " | " | $\underset{H}{-N}-\overset{O}{\overset{\|}{C}}-$ | 194* |
| " | Br— | " | Br— | " | $-N\underset{OCOCH(CH_3)_2}{\underset{|}{-}}N\underset{OCOCH(CH_3)_2}{\underset{|}{-}}$ | 21 |
| " | $O_2N$—(C_6H_3)(CCl_3)—S— | " | Cl— | " | —N=N— | 145 (decomposes) |
| " | " | " | " | " | $\underset{H}{-N}-\overset{O}{\overset{\|}{C}}-$ | * |

-continued

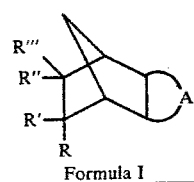
Formula I

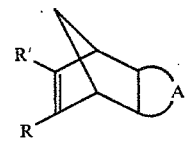
Formula II

| Formula | R | R' | R'' | R''' | A | m.p. [°C] |
|---|---|---|---|---|---|---|
| " | " | " | " | " | -N(COOCH₃)-N(COOCH₃)- | * |
| " | CF₃-S- | " | " | " | " | * |
| " | " | " | " | " | -N(SCF₃)-N(COOCH₃)- | * |
| " | 2-NO₂-C₆H₄-S- | " | " | " | -N(S-C₆H₄-2-NO₂)-N(COOCH₃)- | * |
| " | " | " | " | " | -N-C(=O)-S-C₆H₄-2-NO₂ | * |
| " | CF₃-S- | " | " | " | -N-C(=O)-S-CF₃ | * |
| " | I- | " | N₃- | " | -N(COOCH₃)-N(COOCH₃)- | 11 |
| " | " | " | " | " | -N=N- | * |
| " | " | " | {SCN- und NCS-} | " | -N(COOCH₃)-N(COOCH₃)- | * |
| " | O₂N- | " | {O₂N- und HO-} | " | " | * |
| " | " | " | Cl- | " | -N=N- | * |
| " | 4-Br-C₆H₄-NH- | " | Cl- | " | " | 193 (decomposes) |
| " | " | " | I- | " | " | 183 (decomposes) |
| " | " | " | HO- | " | " | 214 (decomposes) |
| " | C₆H₅-NH- | " | Br- | " | " | |
| " | " | " | I- | " | " | |
| " | 4-Br-C₆H₄-NH- | " | CH₃-COO- | " | " | 166 (decomposes) |
| " | " | " | " | " | -N(COOCH₃)-N(COOCH₃)- | |
| " | 4-Cl-C₆H₄-NH- | " | Cl- | " | -N=N- | 158 (decomposes) |
| " | " | " | F- | " | " | |
| " | " | " | Br- | " | -N(COOCH₃)-N(COOCH₃)- | 110 |
| " | " | " | F- | " | " | |
| " | " | " | Br- | " | -N(COOC₆H₅)-N(COOC₆H₅)- | 95 |

-continued

| | Formula I | | | | Formula II | |
|---|---|---|---|---|---|---|
| Formula | R | R' | R'' | R''' | A | m.p. [°C.] |
| " | " | " | " | " | −N−−−−−N−<br>    |           |<br>COOCH$_2$C$_6$H$_5$  COOCH$_2$C$_6$H$_5$ | 90 |
| " | " | " | I− | " | −N−−−−−N−<br>   |         |<br>SO$_2$C$_6$H$_5$  COOCH$_3$ | * |
| " | Cl−C$_6$H$_4$−NH− | " | Cl− | " | −N−−−−−N−<br>   |       |<br>OCNHCH$_3$  COOCH$_3$ | * |
| " | " | " | HO− | " | " | * |
| " | " | " | " | " | −N=N− | 216 (decomposes) |
| " | CH$_3$−SO$_2$−NH− | " | Br− | " | " | |
| " | C$_6$H$_5$−SO$_2$−NH− | " | I− | " | " | |
| " | CH$_3$−C$_6$H$_4$−NH− | " | Br− | " | " | 161 (decomposes) |
| " | " | " | Cl− | " | " | 143 (decomposes) |
| " | C$_6$H$_5$−SO$_2$−NH− | " | Br− | " | −N−−−−−N−<br>  |       |<br>COOCH$_3$  COOCH$_3$ | |
| " | C$_6$H$_{11}$−SO$_2$−NH− | " | " | " | " | |
| " | 3-CF$_3$-C$_6$H$_4$−NH− | " | " | " | −N=N− | 148 (decomposes) |
| " | " | " | I− | " | " | 146 (decomposes) |
| " | 2-Cl-4-O$_2$N-C$_6$H$_3$−NH− | " | Br− | " | −N−−−−−N−<br>  |       |<br>COOCH$_3$  COOCH$_3$ | 239 (decomposes) |
| " | (C$_6$H$_5$O)$_2$P(O)−NH− | " | " | " | " | |
| " | " | " | " | " | −N=N− | |
| " | (C$_6$H$_5$CH$_2$O)$_2$P(O)−NH− | " | Cl− | " | " | |
| " | " | " | I− | " | −N−−−−−N−<br>  |       |<br>COOCH$_3$  COOCH$_3$ | |
| " | 4-pyridyl−NH− | " | Cl− | " | −N=N− | 100 (decomposes) |
| " | 2-thiazolyl−NH− | " | Br− | " | " | 151 (decomposes) |
| " | " | " | " | " | −N−−−−−N−<br>  |       |<br>COOCH$_3$  COOCH$_3$ | |
| " | " | " | Cl− | " | −N=N− | 153 (decomposes) |
| " | " | " | I− | " | " | 95 |
| " | C$_6$H$_5$−C(O)−NH− | " | Br− | " | " | |
| " | CH$_3$−O−C(O)−NH− | " | Cl− | " | " | |

-continued

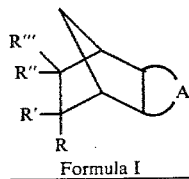
Formula I

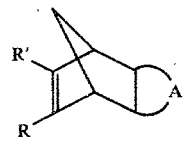
Formula II

| Formula | R | R' | R'' | R''' | A | m.p. [°C] |
|---|---|---|---|---|---|---|
| " | " | " | Br— | " | —N———N—<br>   \|        \|<br>COOCH₃ COOCH₃ | |
| " | 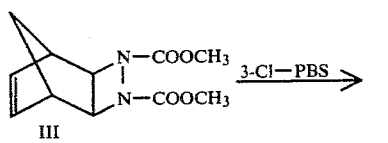 | " | Cl— | " | —N=N— | 204 (decomposes) |
| " | " | " | Br— | " | " | 206 (decomposes) |
| " | 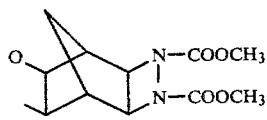  H<br>CH₃—N— | " | Br— | " | " | |
| " | H<br>C₆H₁₁—N— | " | " | " | " | |
| " | " | " | " | " | —N———N—<br>   \|        \|<br>COOCH₃ COOCH₃ | |

*position isomers

EXAMPLE 6

A.

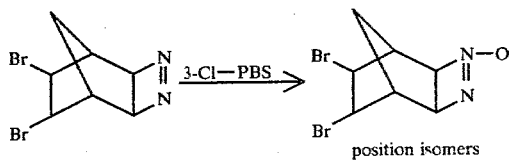

30 parts of III and 43.5 parts of 3-chloroperbenzoic acid (3-Cl-PBS, 70% strength) are stirred for 6 hours in 800 parts of 1,1,2-trichloroethane at 70° C. After cooling, the solution is filtered and extracted with 250 parts of each of a saturated aqueous KI, Na₂S₂O₃ and a NaHCO₃ solution. The organic phase is dried with MgSO₄ and concentrated at 25° C. and 15 mm Hg. The residue is washed with 100 parts of petroleum ether. Yield: 27.8 parts (87% of theory). Melting point: 130° C. (benzene/ligroin).

B.

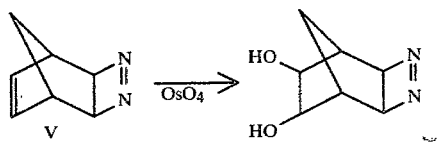
position isomers 1.5 parts of the dibromo derivative of V and 2.7 parts of 3-chlorobenzoic acid (70% strength) are stirred for 2 hours in 20 parts of 1,1,2-trichloroethane at 70° C. After cooling, the solution is filtered and extracted with 30 parts of each of a saturated aqueous KI, Na₂S₂O₃ and a NaHCO₃ solution. The organic phase is dried with MgSO₄ and concentrated at 25° C. and 15 mm Hg. The residue is washed with 10 parts of petroleum ether. Yield: 1.2 parts (78% of theory). Melting point: 116° C.

C.

1.4 parts of V and 3 parts of OsO₄ are stirred in 50 parts of ether for 16 hours. The residue is filtered and stirred with 3 parts of mannite and 30 parts of 10% strength KOH for 3 hours. The mixture is then extracted for 48 hours with 200 parts of dichloromethane. The organic phase is concentrated at 30° C. and 20 mbars. Yield: 1.1 parts (52% of theory). Melting point: 153° C. (decomposes).

The following compounds were prepared in a manner similar to that described in Example 6:

| Formula | R | R' | A | m.p. [°C.] |
|---|---|---|---|---|
| I | H— | H— | —N=N— | 169 (decomposes) |
| " | " | " | —N—N—COOC$_6$H$_5$, COOC$_6$H$_5$ | 77 |
| " | " | " | —N—C(=O)—, H | |
| III | Cl— | | —N=N— | 145 (decomposes) |
| " | " | 2-NO$_2$-C$_6$H$_4$-SO$_2$— | —N—N—COOCH$_3$, COOCH$_3$ | |
| I | H— | H— | —N—N—COOCH$_2$C$_6$H$_5$, OCOCH$_2$C$_6$H$_5$ | 60 |
| " | " | " | —N=N(=O)— | 171 |
| III | Cl— | Cl— | —N=N(=O)— | * |
| " | " | CF$_3$—SO$_2$— | —N=N— | |
| " | " | Cl— | " | |
| | 2-NO$_2$-C$_6$H$_4$-SO— | | | |
| I | H— | H— | —N—N—OCOCH(CH$_3$)$_2$, OCOCH(CH$_3$)$_2$ | 52 |
| III | Cl— | 2-NO$_2$-C$_6$H$_4$-SO— | —N—N—COOCH$_3$, COOCH$_3$ | |
| " | " | 2-NO$_2$-C$_6$H$_4$-SO$_2$— | —N=N(=O)— | 199 * (decomposes) |
| " | " | " | —N—C(=O)—, H | * |
| " | " | CFCl$_2$—SO$_2$— | —N=N— | |
| I | H— | H— | —N—N—COOCH$_3$, OC—N(H)—C$_6$H$_5$ | 147 |
| II | Br— | " | —O— | 20 * |
| " | Cl— | " | " | * |
| III | | Cl— | —N=N— | |
| | 4-O$_2$N, 2-CCl$_3$-C$_6$H$_3$-SO$_2$— | | | |
| " | " | " | —N=N(=O)— | * |
| " | " | " | —N—N—COOCH$_3$, COOCH$_3$ | |

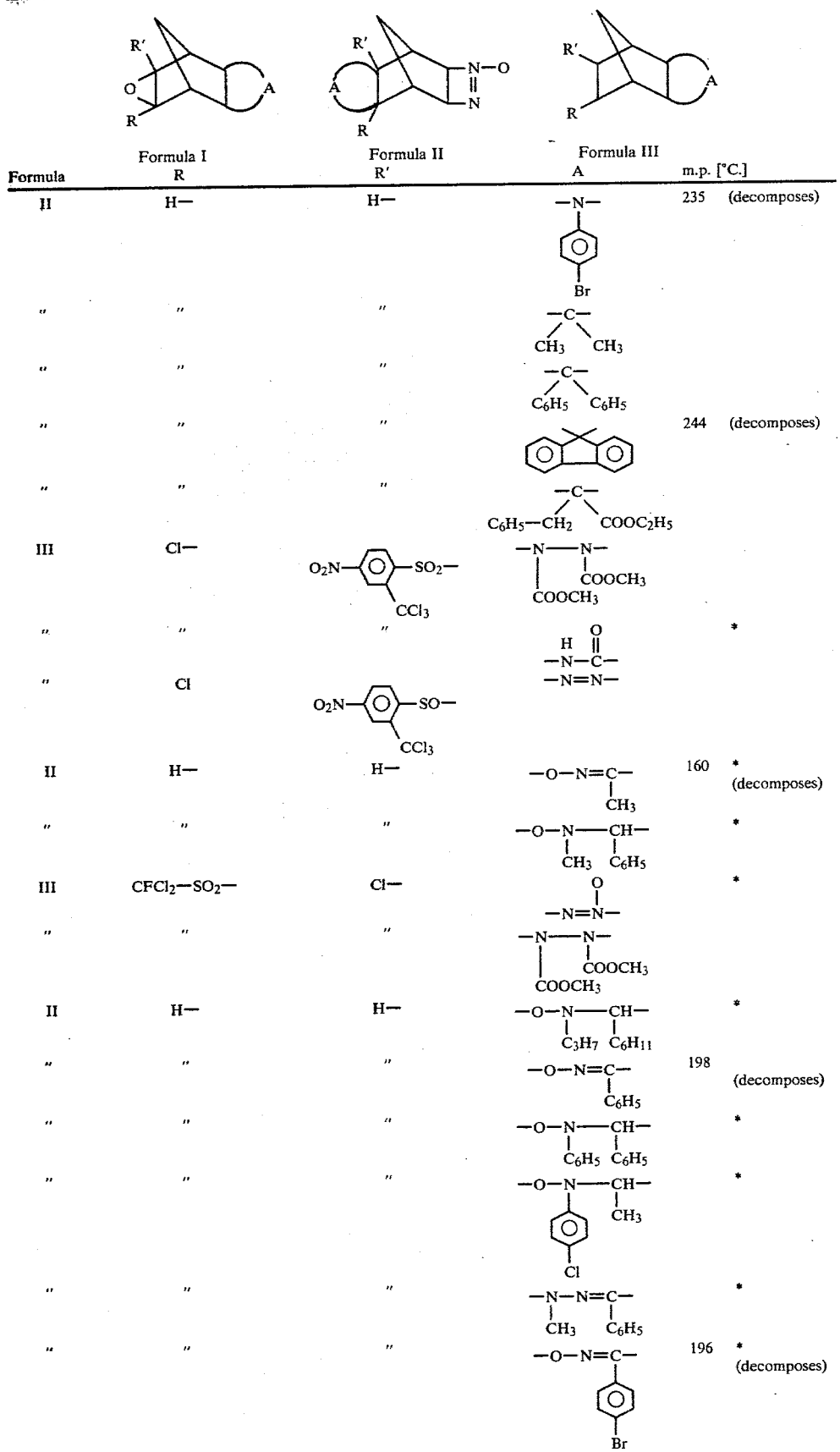

-continued

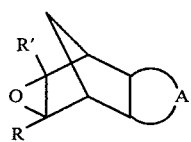 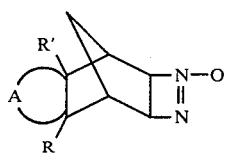 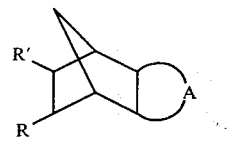

Formula I      Formula II      Formula III

| Formula | R | R' | A | m.p. [°C.] |
|---|---|---|---|---|
| " | " | " | $-N-N=C-$<br>$\quad\|\quad\quad\quad\|$<br>$\;C_6H_5\;\;C_6H_5$ | * |
| " | " | " | $-N-N=C-$<br>$\quad\|\quad\quad\quad\|$<br>(4-Cl-C$_6$H$_4$)(4-Cl-C$_6$H$_4$) | * |
| " | " | " | $-N-N=C-$<br>$\quad\|\quad\quad\quad\|$<br>$\;CH_3\;\;\;\;$thienyl | * |
| " | " | " | $\left\{\begin{array}{l}-N=N-C-\\\;\;\;\;\;\;\;\|\;\;\;\;/\;\;\backslash\\\;\;\;\;\;\;\;O\;\;C_6H_5\;C_6H_5\\\text{and}\\-N=N\;\;\;\;\;-C-\\\;\;\;\;\;\;\;\|\;\;\;\;/\;\;\backslash\\\;\;\;\;\;\;\;O\;\;C_6H_5\;C_6H_5\end{array}\right\}$ | 249 (decomposes) * |
| III | Cl— | CF$_3$—SO$_2$— | $\begin{array}{c}O\\\|\\-N=N-\end{array}$ | * |
| " | " | " | $-N-N-$<br>$\;\|\;\;\;\;\;\;\;\;\|$<br>$\;\;\;\;\;\;\;\;\;COOCH_3$<br>$COOCH_3$ | |
| " | " | CFCl$_2$—SO— | " | |
| " | " | CF$_3$—SO— | $-N=N-$ | |
| " | " | " | $-N-N-$<br>$\;\|\;\;\;\;\;\;\;\;\|$<br>$\;\;\;\;\;\;\;\;\;COOCH_3$<br>$COOCH_3$ | |
| " | " | " | $-N=N-$ | |
| " | $\begin{array}{c}O\\\|\\C_6H_5-C-O-\end{array}$ | $\begin{array}{c}O\\\|\\C_6H_5-C-O-\end{array}$ | $\begin{array}{c}O\\\|\\-N=N-\end{array}$ | |
| " | $\begin{array}{c}O\\\|\\CH_3-C-O-\end{array}$ | $\begin{array}{c}O\\\|\\CH_3-C-O-\end{array}$ | " | |
| " | $\begin{array}{c}H\;\;O\\\|\;\;\|\\CH_3-N-C-O-\end{array}$ | $\begin{array}{c}H\;\;O\\\|\;\;\|\\CH_3-N-C-O-\end{array}$ | " | |
| " | $\begin{array}{c}H\;\;O\\\|\;\;\|\\C_6H_5-N-C-O-\end{array}$ | $\begin{array}{c}H\;\;O\\\|\;\;\|\\C_6H_5-N-C-O-\end{array}$ | " | |
| " | $\begin{array}{c}H\;\;S\\\|\;\;\|\\CH_3-N-C-O-\end{array}$ | $\begin{array}{c}H\;\;S\\\|\;\;\|\\CH_3-N-C-O-\end{array}$ | " | |
| " | $\begin{array}{c}O\\\|\\(CH_3O)_2P-O-\end{array}$ | $\begin{array}{c}O\\\|\\(CH_3O)_2P-O-\end{array}$ | " | |
| " | $\begin{array}{c}S\\\|\\(C_6H_5O)_2P-O-\end{array}$ | $\begin{array}{c}S\\\|\\(C_6H_5O)_2P-O-\end{array}$ | " | |
| " | $\begin{array}{c}CH_3O\;\;\;O\\\;\;\;\;\;\backslash\;\;\|\\\;\;\;\;\;\;\;\;P-O-\\\;\;\;\;/\\\;\;C_6H_5\end{array}$ | $\begin{array}{c}CH_3O\;\;\;O\\\;\;\;\;\;\backslash\;\;\|\\\;\;\;\;\;\;\;\;P-O-\\\;\;\;\;/\\\;\;C_6H_5\end{array}$ | " | |

*position isomers

EXAMPLE 7

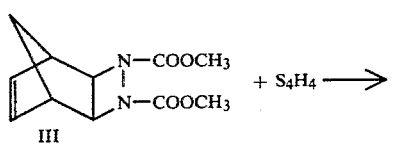 + S₄H₄ ⟶

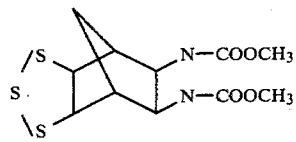

23.8 parts of III and 18.4 parts of S₄N₄ are heated at 110° C. for 24 hours in 150 parts of toluene. After cooling, the reaction mixture is concentrated almost to dryness at 0° C. and 5 mm Hg and the residue is recrystalized from ligroin. Yield: 18.4 parts (55% of theory). Melting point: 210° C. (decomposes).

The following compounds were prepared in the same way:

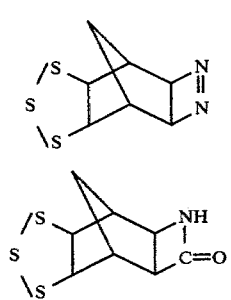

m.p. 125° C. (decomposes)

EXAMPLE 8

Manufacture of starting materials (not in accordance with the invention)

A.

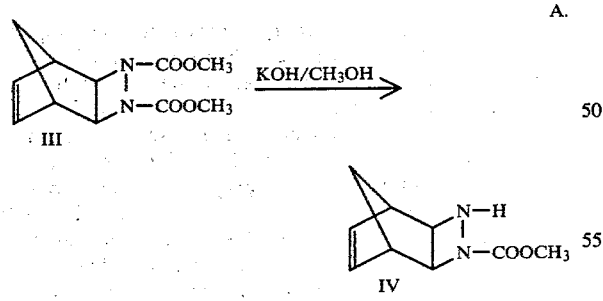

While stirring and at 65° C., a solution of 35 parts of KOH in 60 parts of methanol is dripped into 60 parts of compound III and 50 parts of methanol. The reaction mixture is then stirred for 2 hours at 65° C. The solvent is then distilled off at 50 mbars and the residue extracted several times with a total of 1,200 parts of ether. After the ether has been distilled off, there is obtained 38 parts (85% of theory) of compound VI; m.p.: 94° C. (from ligroin).

B.

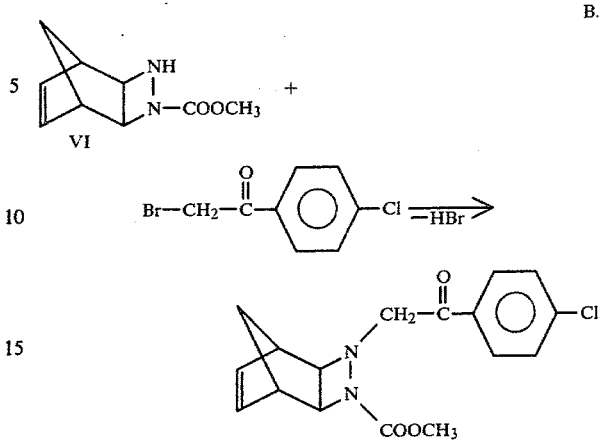

5 parts of compound VI, 7 parts of p-chlorobromoacetophenone and 3 parts of soda are stirred in 150 parts of ether for 24 hours at 34° C. After filtration of the inorganic salts, the solvent and the residue are washed with 50 parts of petroleum ether. Yield: 9.5 parts (91% of theory). Melting point: 111° C. (benzene/ligroin).

C.

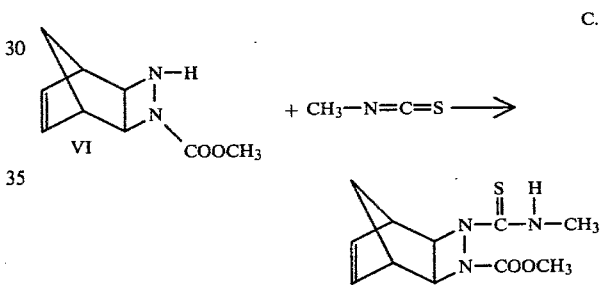

17 parts of compound VI and 8.7 parts of methylmustard oil are heated in 200 parts of benzene for 5 hours at 80° C. After the solvent has been distilled off, the residue is washed with 100 parts of petroleum ether. Yield: 25 parts (97% of theory). Melting point: 116° C. (ethanol/ligroin).

D.

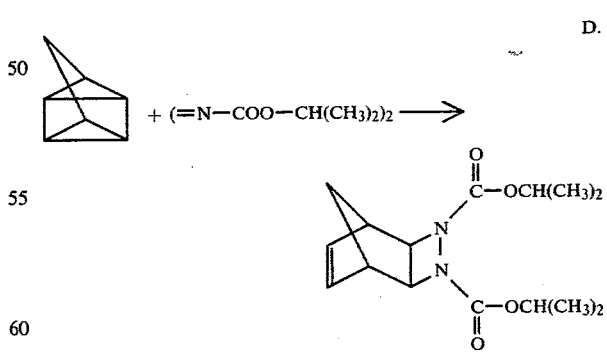

At 80° C., 40.5 parts of azodicarboxylic acid dissopropyl ester is dripped into 20 parts of quadricyclane in 100 parts of benzene. The mixture is then heated for 24 hours at 80° C. and the solvent is then removed at 50 mbars. Yield: 58 parts (98% of theory). Melting point: 41° C.

The following compounds were prepared in the same way:

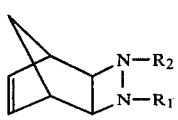

| R₁ | R₂ | m.p. [°C] |
|---|---|---|
| H— | $-\overset{O}{\underset{}{\overset{\|}{C}}}-\overset{H}{\underset{}{N}}-CH_3$ | 163 (decomposes) |
| —CH₂—COOCH₃ | —COOCH₃ | 76 |
| —SO₂—C₆H₅ | " | 130 |
| $-\overset{O}{\underset{}{\overset{\|}{C}}}-\langle O \rangle-Cl$ | " | 128 |
| $-\overset{O}{\underset{}{\overset{\|}{C}}}-\overset{H}{\underset{}{N}}-C_6H_5$ | " | 141 |
| $-\overset{S}{\underset{}{\overset{\|}{C}}}-\overset{H}{\underset{}{N}}-C_6H_5$ | " | 164 (decomposes) |
| $-\overset{O}{\underset{}{\overset{\|}{C}}}-\overset{H}{\underset{}{N}}-CH_3$ | " | 128 |
| $-\underset{OHC-CH_3}{\overset{H}{\underset{\|}{}}}$ | " | b.p. (1 mbar) 100 |
| $-\overset{O}{\underset{}{\overset{\|}{C}}}-S-CH_2-\overset{Cl}{\underset{}{\overset{\|}{C}}}=CCl_2$ | " | 73 |
| $-\overset{O}{\underset{}{\overset{\|}{C}}}-S-CH_2-C_6H_5$ | " | 75 |
| $-\overset{O}{\underset{}{\overset{\|}{C}}}-(CH_2)_7-\overset{H}{\underset{}{C}}=\overset{H}{\underset{}{C}}-(CH_2)_7-CH_3$ | " | −10 |
| $-CH_2-\overset{N}{\underset{O}{\overset{\|}{\diagdown}}}\overset{}{\underset{N}{\diagup}}\overset{Cl}{\langle O \rangle}$ | " | 135 |
| $C_6H_5-O-\overset{O}{\underset{}{\overset{\|}{C}}}-$ | $C_6H_5-O-\overset{O}{\underset{}{\overset{\|}{C}}}-$ | 98 |
| $C_6H_5-CH_2-O-\overset{O}{\underset{}{\overset{\|}{C}}}-$ | $C_6H_5-CH_2-O-\overset{O}{\underset{}{\overset{\|}{C}}}-$ | 12 |

The compounds described in Example 8 and the table pertaining thereto may be used as starting compounds for the synthesis of active ingredients (cf. tables in Examples 1, 2, 4, 5, 6 and 7).

The new active ingredients have a strong biological action on plants, i.e., they influence plant growth, either by reducing growth height, by changing the concentration of plant materials, or by destroying unwanted plants while leaving crop plants unaffected.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol, ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alochol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients oils of various types, herbicides, fungicides, nematocides, insecticides, bactericides, trace elements, fertilizers, antifoams (e.g., silicones), and other growth regulators.

In various cases, it may prove advantageous to combine or mix the compounds according to the invention with other growth-regulating active ingredients, e.g., ethylene-forming compounds of various chemical structures (such as phosphonic acid derivatives, silanes, ethyl hydrazines), and onium compounds (such as trimethylammonium, hydrazonium and sulfonium salts, and derivatives of morpholinium, piperidinium and pyridazinium compounds). Other growth-regulating substances, e.g., from the group of trifluoromethylsulfonamido-p-acetotoluidides, maleic hydrazide, abscisin derivatives, chlorinated phenoxy fatty acids having an auxin-like action, and polyhydric alcohols and fatty acid esters having a specific action on meristematic tissue.

The application rate of the agents according to the invention may vary, and depends mainly on the type of effect desired; it is generally from 0.1 to 15 more more, but preferably from 0.2 to 6, kg of active ingredient per hectare.

The agents according to the invention influence the growth of plant parts above and below the soil in different ways, and have, at the usual application concentrations, a low toxicity to warmbloods.

The new agents have an effect on the physiology of plants, and may be used for various purposes. The different actions of these active ingredients depend in essence on the time of application, with reference to the development stage of the seed or plant, and on the concentrations employed.

Vegetative and generative plant growth, and—in appropriate concentrations—germination are influenced by the new agents.

The influence on vegetative development is manifested particularly in a reduction in growth height, resulting in many plants, particularly cereals, in increased rigor and a reduced tendency to lodging. Tillering is also improved, which results in a larger number of ear-bearing stems per unit area.

In grass, the reduction in growth height results in a more compact and resistant sward, and especially in a reduction in mowing frequency. This is of great economic advantage with lawns, grass verges and in parks. An additional feature is that, parallel to the reduction in growth height, the chlorophyll content of the plant is also increased; consequently, grass and other plants treated with the new agents take on a much darker green.

The influence on vegetative growth results in numerous plants, e.g., cotton and soybeans, in a considerable increase in flowering and fruiting.

Attention should be drawn in particular to the surprising fact that treatment with the compounds according to the invention induces rooting. This results in more rational utilization of water and nutrients by the treated plants; their resistance to dryness and cold (frost) is also increased.

The agents according to the invention may also find varied and extensive use in fruit crops, the cultivation of ornamentals and landscape gardening, including the influence of vegetation on uncultivated areas, airfields and training areas.

The compounds may also be successfully used to influence blossoming and ripening, and in special cultivation processes.

The new agents may also influence the concentration of important plant materials such as sugar and proteins.

The extent and type of action are dependent on various factors, especially the time of application with reference to the development stage of the plant, and the concentration. These factors in turn vary, depending on the type of plant and the desired effect. Thus, for instance, lawns should be treated during the whole growth period; ornamentals in which it is desired to increase the intensity and number of flowers, before the buds have formed; and plants whose fruit is to be eaten or processed, a sufficient length of time before the harvest. Various derivatives of the class of compounds described here have herbicidal properties. They are therefore suitable for removing unwanted plant growth, or keeping it in check.

EXAMPLE 9

Influence of some polycyclic nitrogenous compounds on the growth height of wheat and barley Spring wheat of the "Opal" variety and spring barley of the "Union" variety were grown in the winter half of the year under greenhouse conditions in plastic dishes 11.5 cm in diameter, in a peat substrate provided with sufficient nutrients.

For the soil (preemergence) treatment, the active ingredients were poured, at two application rates, as aqueous formulations onto the final soil surface after sowing.

The reductions in growth height caused by the treatment were determined by measuring the height of the plants at the end of the experiment after 30 days' growth, and comparing it with that of untreated plants. The prior art active ingredient N,N,N-trimethyl-N-$\beta$-chloromethylammonium chloride (CCC, German Printed Application DAS No. 1,294,734) was also used for comparison purposes.

The individual results are given in the table below.

| Influence on the growth height of spring wheat Soil treatment | | | |
|---|---|---|---|
| | Appln. rate | Plant height | |
| Active Ingredient | kg/ha | cm | % |
| Control (untreated) | — | 30.0 | 100 |
| CCC (prior art) | 3 | 21.5 | 71.7 |
| | 12 | 19.5 | 65.0 |
| 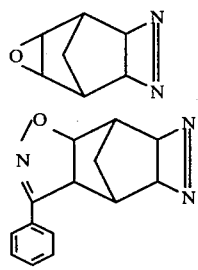 | 3 | 21.5 | 71.7 |
| | 12 | 12.5 | 41.7 |
| 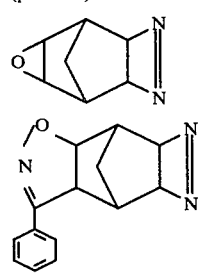 | 3 | 20.0 | 66.7 |
| | 12 | 14.0 | 46.7 |

| Influence on the growth height of spring barley Soil treatment | | | |
|---|---|---|---|
| | Appln. rate | Plant height | |
| Active Ingredient | kg/ha | cm | % |
| Control (untreated) | — | 32.2 | 100 |
| CCC (prior art) | 3 | 27.5 | 85.1 |
| | 12 | 24.5 | 75.9 |
| 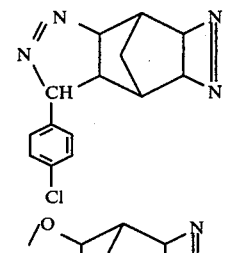 | 3 | 25.0 | 77.4 |
| | 12 | 14.0 | 43.3 |
| 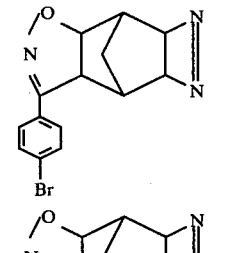 | 3 | 24.5 | 75.9 |
| | 12 | 16.0 | 49.5 |

EXAMPLE 10

Influence of some polycyclic nitrogenous compounds on the growth height of wheat and barley Spring wheat ("Opal" variety) and spring barley ("Union" variety) were grown under greenhouse conditions in plastic dishes 11.5 cm in diameter, in a peat substrate provided with sufficient nutrients. For the soil (preemergence) treatment, the active ingredients were poured, at two application rates, as aqueous formulations onto the surface of the substrate after sowing.

Leaf treatment was effected by spraying the plants at a growth height of 10 cm with aqueous formulations of the active ingredients at two application rates.

The plant height was measured at the end of the experiment. The figures obtained show the shortening effect of the active ingredients under investigation. The prior art compound β-chloroethylphosphonic acid (Ethephon, German Printed Application DAS No. 1,667,968) was used for comparison purposes.

The individual results are given below:

| Influence on the growth height of spring wheat A Soil treatment | | | |
|---|---|---|---|
| | Appln. rate | Plant height | |
| Compound | kg/ha | cm | % |
| Control (untreated) | — | 32.0 | 100 |
| Ethephon (prior art) | 3 | 29.0 | 90.6 |
| | 12 | 25.0 | 78.1 |
| 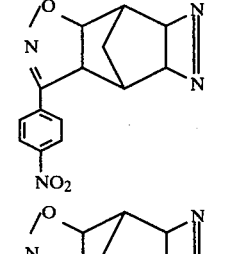 | 3 | 17.0 | 53.1 |
| | 12 | 14.0 | 43.8 |
| 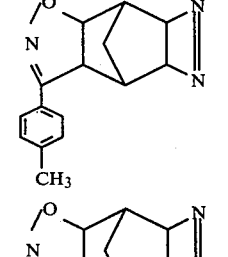 | 3 | 26.5 | 82.8 |
| | 12 | 25.5 | 79.7 |
| 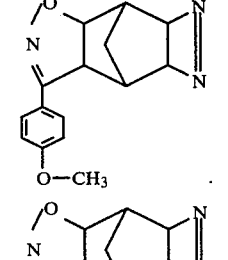 | 3 | 25.5 | 79.7 |
| | 12 | 22.0 | 68.8 |
| 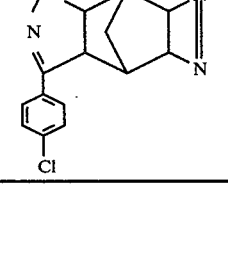 | 3 | 23.5 | 73.4 |
| | 12 | 22.0 | 68.8 |
| | 3 | 27.0 | 84.4 |
| | 12 | 24.5 | 76.6 |
| 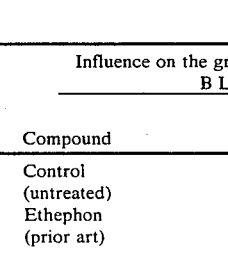 | 3 | 16.0 | 50.0 |
| | 12 | 15.0 | 46.9 |

| Influence on the growth height of spring wheat B Leaf treatment | | | |
|---|---|---|---|
| | Appln. rate | Plant height | |
| Compound | kg/ha | cm | % |
| Control (untreated) | — | 32.8 | 100 |
| Ethephon (prior art) | 1.5 | 30.0 | 91.5 |
| | 6.0 | 25.0 | 76.2 |

-continued
Influence on the growth height of spring wheat
B Leaf treatment

| Compound | Appln. rate kg/ha | Plant height cm | Plant height % |
|---|---|---|---|
| [4-Cl-C6H4-CH=N-N= bridged bicyclic diazine] | 1.5 | 23.5 | 71.6 |
|  | 6.0 | 22.0 | 67.1 |
| [4-Br-C6H4-C(=N-O)- bridged bicyclic diazine] | 1.5 | 29.0 | 88.4 |
|  | 6.0 | 27.5 | 83.8 |
| [4-NO2-C6H4-C(=N-O)- bridged bicyclic diazine] | 1.5 | 29.0 | 88.4 |
|  | 6.0 | 27.0 | 82.3 |
| [4-CH3-C6H4-C(=N-O)- bridged bicyclic diazine] | 1.5 | 29.5 | 89.9 |
|  | 6.0 | 27.5 | 83.3 |
| [4-Cl-C6H4-C(=N-O)- bridged bicyclic diazine] | 1.5 | 29.0 | 88.4 |
|  | 6.0 | 27.0 | 82.3 |
| [3-CF3-C6H4-NH- iodo bridged bicyclic diazine] | 1.5 | 27.5 | 83.3 |
|  | 6.0 | 25.5 | 77.7 |

Influence on growth height of spring barley
A Soil treatment

| Compound | Appln. rate kg/ha | Plant height cm | Plant height % |
|---|---|---|---|
| Control (untreated) | — | 34.3 | 100 |
| Ethephon (prior art) | 3 | 32.0 | 93.3 |
|  | 12 | 27.5 | 80.2 |
| [4-Cl-C6H4-CH=N-N= bridged bicyclic diazine] | 3 | 22.0 | 64.1 |
|  | 12 | 20.0 | 58.3 |
| [4-Br-C6H4-C(=N-O)- bridged bicyclic diazine] | 3 | 28.0 | 81.6 |
|  | 12 | 26.0 | 75.8 |
| [4-NO2-C6H4-C(=N-O)- bridged bicyclic diazine] | 3 | 27.0 | 78.8 |
|  | 12 | 24.0 | 70.0 |
| [4-CH3-C6H4-C(=N-O)- bridged bicyclic diazine] | 3 | 25.0 | 72.9 |
|  | 12 | 21.0 | 61.2 |
| [4-OCH3-C6H4-C(=N-O)- bridged bicyclic diazine] | 3 | 30.0 | 87.5 |
|  | 12 | 29.0 | 84.5 |
| [4-Cl-C6H4-C(=N-O)- bridged bicyclic diazine] | 3 | 26.0 | 75.8 |
|  | 12 | 24.0 | 70.0 |

| Influence on growth height of spring barley | | | |
|---|---|---|---|
| B Leaf treatment | | | |
| | Appln. rate | Plant height | |
| Compound | kg/ha | cm | % |
| Control (untreated) | — | 28.0 | 100 |
| Ethephon (prior art) | 1.5 | 27.0 | 96.4 |
| | 6.0 | 24.5 | 87.5 |
| 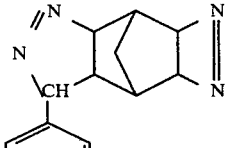 | 1.5 | 22.0 | 78.6 |
| | 6.0 | 19.5 | 69.6 |
| 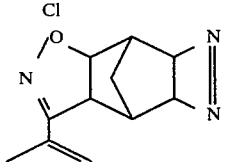 | 1.5 | 25.5 | 91.1 |
| | 6.0 | 25.0 | 89.3 |
| 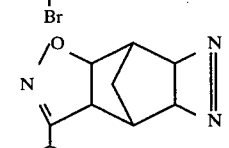 | 1.5 | 25.0 | 89.3 |
| | 6.0 | 24.5 | 87.5 |
| 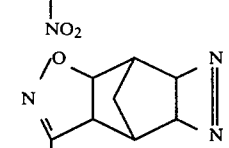 | 1.5 | 25.5 | 91.1 |
| | 6.0 | 25.0 | 89.3 |
| 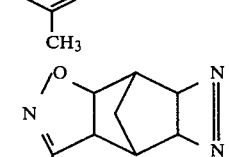 | 1.5 | 26.0 | 92.9 |
| | 6.0 | 24.5 | 87.5 |
| 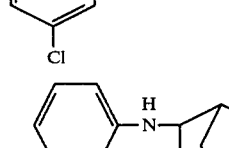 | 1.5 | 25.0 | 89.3 |
| | 6.0 | 24.0 | 85.7 |

EXAMPLE 11

Influence of some polycyclic nitrogenous compounds on the growth height of wheat, barley and rye The test plants—spring wheat ("Opal" variety), spring barley ("Union" variety) and spring rye ("Petkuser" variety)—were grown under greenhouse conditions in plastic dishes 11.5 cm in diameter, in a peat substrate provided with sufficient nutrients.

The soil (preemergence) treatment was effected after sowing by pouring aqueous formulations of the active ingredients, at four application rates, onto the surface of the substrate.

Leaf treatment was effected by spraying the plants at a growth height of 11 cm with aqueous formulations of the active ingredients, at three application rates.

The shortening effect caused by the compounds was shown by measurements of the height of the plants at the end of the experiment.

The prior art compound N,N,N-trimethyl-N-β-chloroethylammonium chloride (CCC, German Printed Application DAS No. 1,294,734) was used for comparison purposes.

The individual results are given below:

| Influence on the growth height of spring wheat | | | |
|---|---|---|---|
| Leaft treatment | | | |
| | Appln. rate | Plant height | |
| Compound | kg/ha | cm | % |
| Control (untreated) | — | 30.8 | 100 |
| CCC (prior art) | 0.75 | 27.5 | 89.3 |
| | 1.50 | 26.0 | 84.4 |
| | 3.00 | 25.0 | 81.2 |
| 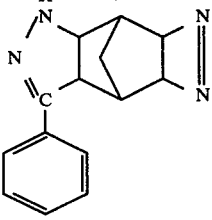 | 0.75 | 26.5 | 86.0 |
| | 1.50 | 25.5 | 82.8 |
| | 3.00 | 24.0 | 77.9 |

| Influence on the growth height of spring barley | | | |
|---|---|---|---|
| A Soil treatment | Appln. rate | Plant height | |
| Compound | kg/ha | cm | % |
| Control (untreated) | — | 32.8 | 100 |
| CCC (prior art) | 0.75 | 29.5 | 89.9 |
| | 1.50 | 29.5 | 89.9 |
| | 3.00 | 27.5 | 83.8 |
| | 6.00 | 26.0 | 79.3 |
| 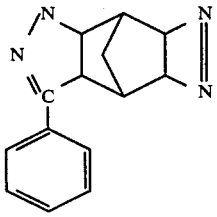 | 0.75 | 32.0 | 97.6 |
| | 1.50 | 28.0 | 85.4 |
| | 3.00 | 27.0 | 82.3 |
| | 6.00 | 23.0 | 70.1 |

| B Leaf treatment | | | |
|---|---|---|---|
| | Appln. rate | Plant height | |
| Compound | kg/ha | cm | % |
| Control (untreated) | — | 27.8 | 100 |
| CCC (prior art) | 0.75 | 27.5 | 98.4 |
| | 1.50 | 27.0 | 97.1 |

-continued

| B Leaf treatment Compound | Appln. rate kg/ha | Plant height cm | % |
|---|---|---|---|
| 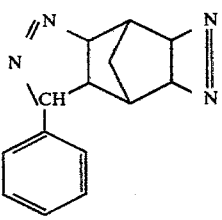 | 3.00 | 27.0 | 97.1 |
|  | 0.75 | 23.5 | 84.5 |
|  | 1.50 | 23.0 | 82.7 |
|  | 3.00 | 21.5 | 77.3 |
| 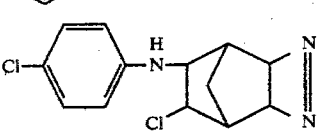 | 0.75 | 26.0 | 93.5 |
|  | 1.50 | 25.5 | 91.7 |
|  | 3.00 | 23.5 | 84.5 |

| Influence on the growth height of spring rye | | | |
|---|---|---|---|
| A Soil treatment Compound | Appln. rate kg/ha | Plant height cm | % |
| Control (untreated) | — | 32.3 | 100 |
| CCC (prior art) | 0.75 | 31.5 | 97.5 |
|  | 1.50 | 30.5 | 94.4 |
|  | 3.00 | 30.0 | 92.9 |
|  | 6.00 | 28.5 | 88.2 |
| 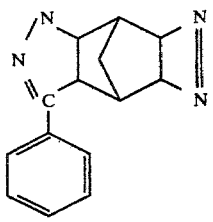 | 0.75 | 30.0 | 92.9 |
|  | 1.50 | 26.5 | 82.0 |
|  | 3.00 | 25.0 | 77.4 |
|  | 6.00 | 23.0 | 71.2 |
| 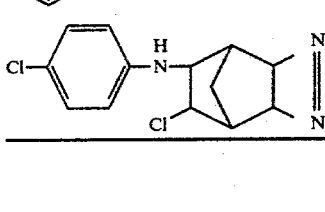 | 0.75 | 28.0 | 86.7 |
|  | 1.50 | 27.0 | 83.5 |
|  | 3.00 | 25.0 | 77.4 |
|  | 6.00 | 23.0 | 71.2 |

| B Leaf treatment Compound | Appln. rate kg/ha | Plant height cm | % |
|---|---|---|---|
| Control (untreated) | — | 28.5 | 100 |
| CCC (prior art) | 0.75 | 27.0 | 94.7 |
|  | 1.50 | 25.5 | 89.5 |
|  | 3.00 | 25.5 | 89.5 |
| 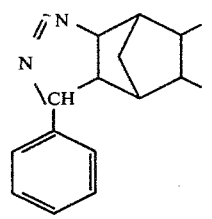 | 0.75 | 23.0 | 80.7 |
|  | 1.50 | 20.5 | 71.9 |
|  | 3.00 | 20.5 | 71.9 |
| 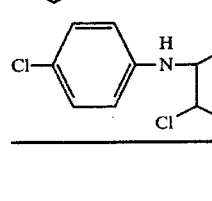 | 0.75 | 25.5 | 89.5 |
|  | 1.50 | 24.5 | 86.0 |
|  | 3.00 | 24.5 | 86.0 |

EXAMPLE 12

Action on grass or lawns

In an experiment in large vessels, lawn seed of the following standard composition was sown in a loamy soil: Agrostis tenuis (10%), Cynosurus cristatus (10%), Festuca rubra (15%), Lolium perenne (35%) and Poa pratensis (30%). 1.5 g of N as ammonium nitrate and 1 g of $P_2O_5$ as secondary potassium phosphate were applied as fertilizer. After the grass had been cut twice, the active ingredients were sprayed in conventional manner at various application rates onto the grass which was 4 cm high. The growth height and the mowings were determined 19 days after the treatment. Compared with the control, the treated plants reacted with most considerable height reductions and a proportionate decrease in mowings.

The data below also demonstrate the lasting action of the agents investigated.

| | | Influence on the growth height of, and amount of mowings in, gass | | | | | | |
|---|---|---|---|---|---|---|---|---|
| | Appln. rate kg/ha | First mowing | | | | Second mowing | | |
| | | Growth height | | Mowings | | Growth height | | Mowings |
| Compound | | cm | relative | g | relative | cm | relative | g | relative |
| Control | — | 21.8 | 100 | 134.2 | 100 | 20.0 | 100 | 90.6 | 100 |
| 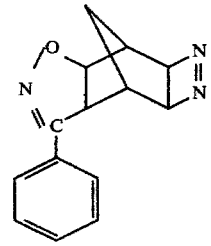 | 3.0 | 20.0 | 91.7 | 116.3 | 86.7 | 19.0 | 95.0 | 94.8 | 104.6 |
|  | 6.0 | 17.0 | 78.0 | 101.1 | 75.3 | 16.5 | 82.5 | 85.2 | 94.0 |

-continued

| | Appln. rate | First mowing | | | | Second mowing | | | |
|---|---|---|---|---|---|---|---|---|---|
| | | Growth height | | Mowings | | Growth height | | Mowings | |
| Compound | kg/ha | cm | relative | g | relative | cm | relative | g | relative |
| 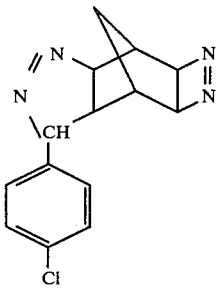 | 3.0 | 20.0 | 91.7 | 125.1 | 93.2 | 19.0 | 95.0 | 89.9 | 99.2 |
| | 6.0 | 18.0 | 82.6 | 119.0 | 88.7 | 19.0 | 95.0 | 92.2 | 101.8 |
| 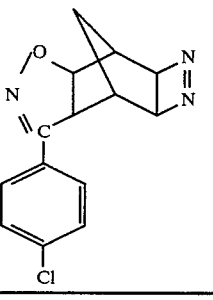 | 3.0 | 21.0 | 96.3 | 117.7 | 87.7 | 18.5 | 92.5 | 75.3 | 83.1 |
| | 6.0 | 18.5 | 84.9 | 114.0 | 84.9 | 17.0 | 85.0 | 72.1 | 79.6 |

EXAMPLE 13

Experiments demonstrating the growth-regulating or herbicidal action

To demonstrate the effectiveness of the new compounds, greenhouse experiments were carried out as follows. Plastic flowerpots having a volume of 300 cm³ were filled with a sandy loam and the test plants placed therein (either as seed, as vegetatively reproduced species, or as potted plants, e.g., vines). For preemergence treatment, the active ingredients were suspended or emulsified in water as vehicle and sprayed onto the surface of the soil immediately after sowing by means of finely distributing nozzles. The potted vines were treated by spraying them with the correspondingly diluted liquor. For postemergence treatment, the agents were, as stated above, sprayed in water onto the leaves of the test plants, some liquor also falling onto the soil. In some special cases, solid active ingredients were first dissolved in dimethylformamide and then applied in a total liquor amount of 400 liters of water per hectare. For the postemergence treatment, the plants were first grown to a height of from 3 to 10 cm before being treated. With grasses, the first growth was cut, and the new growth treated 2 to 3 days after cutting. The temperature requirements of the plants were taken into account by placing them in cooler or warmer sections of the greenhouse. The experiments were run for from 4 to 6 weeks, during which time the plants were tended and their reaction to the various treatments was assessed.

The application rates are given in kg/ha of active ingredient, regardless of the method of application and the amount of water used.

A 0 to 100 scale was used for the evaluation, 0 denoting normal emergence or no damage (or no inhibition), and 100 denoting non-emergence or complete destruction of the plants. A distinction should be made in the influence on growth between desired changes without any appreciable disadvantageous phytotoxic effects (e.g., purely growth-regulating effects) and those of a phytotoxic herbicical character.

The results are given in the tables below.

| List of plant species | |
|---|---|
| Botanical term | Common name |
| Alopecurus myosuroides | Blackgrass |
| Cynodon dactylon | Bermudagrass |
| Cyperus esculentus | Yellow nutsedge |
| Datura stramonium | Jimson weed |
| Digitaria sanguinalis | Hairy crabgrass |
| Echinochloa crus galli | Barnyardgrass |
| Euphorbia spp. usually E. geniculata | Spurge family |
| Eleusine indica | Goosegrass |
| Galium aparine | Catchweed bedstraw |
| Ipomoea spp. usually I. lacunosa | Morningglory |
| Matricaria chamomilla | Wild chamomile |
| Panicum virgatum | Switchgrass |
| Poa annua | Annual bluegrass |
| Setaria faberii | Giant foxtail |
| Sinapis alba | White mustard |
| Solanum nigrum | Black nightshade |
| Sorghum halepense | Johnsongrass |
| Stellaria media | Chickweed |

| Tolerance of new compounds by potted vines in greenhouse; spray application ||||
|---|---|---|---|
| Compound | kg/ha | Change in shoot growth cm | Potted vines - leaf damage |
| 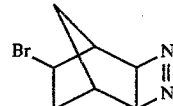 | 4.0<br>8.0 | 14.7<br>13.3 | none |
| 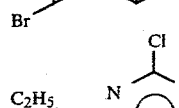<br>prior art | 4.0<br>8.0 | 17.3<br>10.3 | chlorotic yellowing, necroses |
| 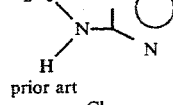<br>prior art | 4.0<br>8.0 | 15.3<br>15.7 | slight chlorosis |
| Untreated control | — | 15.3 | none |

| Influence on shoot growth of various plants; postemergence treatment in the greenhouse |||||
|---|---|---|---|---|
| | | Shoot length (cm) in |||
| Compound | kg/ha | Arachys hypogaea | Oryza sativa | Poa pratensis |
| 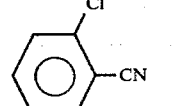 | 1.0<br>2.0<br>4.0 | 10<br>10<br>10 | 16<br>16<br>16 | 2ˣ<br>2ˣ<br>2ˣ |
| Control (untreated) | | 14 | 22 | 4 |
| 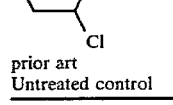<br>prior art | 1.0<br>2.0<br>4.0 | 12<br>5<br>5 | —<br>—<br>— | 4<br>4<br>4 |
| [Cl—CH₂—CH₂—N(CH₃)₃]⁺Cl⁻ | 1.0<br>2.0<br>4.0 | 16<br>16<br>16 | 20<br>20<br>20 | 4<br>4<br>3 |

ˣlimited leaf scorch

| Removal and inhibition of unwanted plants; pre-(PRE)-emergence treatment in the greenhouse |||||||
|---|---|---|---|---|---|---|
| | | Test plants and % damage |||||
| Compound | kg/ha | Cyper. esc. | Echin. c.g. | Lam. spp. | Setar. spp. | Solan. nig. |
| 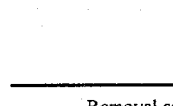 | 2.0 PRE<br>4.0 PRE<br>8.0 PRE | 20<br>55<br>70 | 50<br>80<br>90 | 95<br>95<br>95 | 100<br>100<br>100 | 95<br>95<br>95 |
| 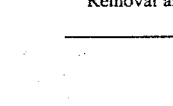 | 2.0 PRE<br>4.0 PRE<br>8.0 PRE | 0<br>0<br>0 | 88<br>90<br>95 | 72<br>90<br>95 | 40<br>100<br>100 | 85<br>85<br>90 |

0 = no damage
100 = complete destruction

| Growth inhibition in lawns caused by new compounds; preemergence treatment in the greenhouse |||
|---|---|---|
| Compound | kg/ha | % growth inhibition after emergence Poa pratensis |
| 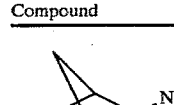 | 0.5<br>1.0<br>2.0<br>4.0 | 50 very short<br>60 growth overall;<br>60 grass compact<br>70 and dark green |
| prior art<br>[Cl—CH₂—CH₂—N(CH₃)₃]⁺Cl⁻ | 0.5<br>1.0<br>2.0<br>4.0 | 0<br>10<br>10<br>10 |

0 = no inhibition
100 = no growth

| Influence on the shoot growth of various plants; postemergence treatment in the greenhouse | | | | | |
|---|---|---|---|---|---|
| | | Shoot length (cm) in | | | |
| Structural formula | kg/ha | Cynodon$^x$ dactylon | Euphorbia geniculata | Hordeum vulgare | Poa pratensis |
| [structure: Cl-C6H4-NH-(bicyclic with N=N)-Cl] | 0.5 | — | 9 | 12.5 | — |
| | 1.0 | 5 | 9 | 12 | — |
| | 2.0 | 5 | 9 | 12 | — |
| [structure: Cl-C6H4-NH-(bicyclic with N=N)-OH] | 0.5 | — | — | 16 | — |
| | 1.0 | 6 | — | 15 | 13 |
| | 2.0 | 6 | — | 14 | 13 |
| $[Cl-CH_2-CH_2-N(CH_3)_3]^\oplus Cl^\ominus$ prior art | 0.5 | — | 12.5 | 14 | — |
| | 1.0 | 7 | 13 | 14 | 20 |
| | 2.0 | 7 | 13 | 14 | 19 |
| Untreated control | — | 8 | 14 | 19 | 20 |

$^x$from seed

| Inhibition of shoot growth by growth regulators; pre-(PRE) and post(POST)-emergence treatment in the greenhouse | | | |
|---|---|---|---|
| | | Test plants and shoot growth inhibition (%) | |
| Structural formula | kg/ha | Euphorbia geniculata | Medicago sativa |
| [structure: O-N=C(phenyl)-bicyclic with N=N] | 0.5 PRE | 33 | — |
| | 1.0 PRE | 40 | — |
| | 2.0 POST | 30 | 20 |
| | 4.0 POST | 30 | 20 |
| $[Cl-CH_2-CH_2-N(CH_3)_3]^\oplus Cl^\ominus$ prior art | 0.5 PRE | 0 | 0 |
| | 1.0 PRE | 0 | 0 |
| | 2.0 POST | 0 | 0 |
| | 4.0 POST | 10 | 0 |

| Influence of growth-regulating compounds on plant growth; pre-(PRE) and post(POST)-emergence treatment in the greenhouse | | | | | | | | |
|---|---|---|---|---|---|---|---|---|
| | | Test plants and % shoot inhibition | | | | | | |
| Structural formula | kg/ha | Arachys hypog. | Glycine max | Euphorbia genic. | Cynodon$^x$ dactyl. | Tritic. aestiv. | Hordeum vulg. | Poa prat. |
| [structure: bicyclic with N=N, N=C-phenyl] | 1.0 PRE | 10 | 10 | 10 | 10 | 30 | 25 | 60 |
| | 2.0 PRE | 10 | 25 | 30 | 10 | 30 | 25 | 60 |
| | 1.0 POST | 20 | — | — | 13 | 10 | 30 | 60 |
| | 2.0 POST | 30 | — | — | 25 | 20 | 30 | 60 |
| $[Cl-CH_2-CH_2-N(CH_3)_3]^\oplus Cl^\ominus$ prior art | 1.0 PRE | 0 | 0 | 0 | 0 | 20 | 20 | 0 |
| | 2.0 PRE | 0 | 0 | 0 | 0 | 20 | 20 | 0 |
| | 1.0 POST | 0 | 0 | 0 | 0 | 30 | 10 | 0 |
| | 2.0 POST | 0 | 0 | 0 | 0 | 30 | 10 | 0 |
| $(CH_3)_2N-NH-C(=O)-CH_2-CH_2-COOH$ prior art | 1.0 PRE | 50 | 0 | 0 | — | — | — | — |
| | 2.0 PRE | 50 | 0 | 0 | — | — | — | — |
| | 1.0 POST | 30 | — | — | 20 | — | — | — |
| | 2.0 POST | 30 | — | — | 20 | — | — | — |

$^x$from seed

| Herbicidal action of new compounds; pre-(PRE) and post (POST)-emergence application in the greenhouse | | | | | | | | |
|---|---|---|---|---|---|---|---|---|
| | | Test plants and % damage | | | | | | |
| Compound | kg/ha | Lolium mult. | Sinapis alba | Menta piper. | Ipom. spp. | Viola tric. | Cynodon dact. (seed) | Euph. gen. |
| [structure: HO, HO-bicyclic with N=N] | 3.0 PRE | 90 | 80 | — | — | — | — | — |
| | 3.0 POST | 95 | — | 100 | 100 | 95 | — | — |

-continued

Herbicidal action of new compounds; pre-(PRE) and post (POST)-emergence application in the greenhouse

| Compound | kg/ha | | | | | | |
|---|---|---|---|---|---|---|---|
| (Br, bicyclic, N=N) | 3.0 POST | — | 100 | — | — | — | — | — |
| (Br, Br, bicyclic, N=N) | 3.0 PRE | 40 | 70 | — | — | — | — | — |
| | 3.0 POST | 100 | 100 | — | — | — | — | — |
| | 1.0 PRE | — | — | — | — | — | 100 | 90 |
| (Cl, Cl, bicyclic, N=N) | 3.0 PRE | 100 | 100 | — | — | — | — | — |
| | 3.0 POST | 60 | 80 | — | — | — | — | — |
| | 1.0 PRE | — | — | — | — | — | 90 | 70 |
| | 2.0 POST | — | — | — | — | — | 100 | 95 |

| | | Test plants and % damage | | | | | |
|---|---|---|---|---|---|---|---|
| Compound | kg/ha | Lolium mult. | Galium apar. | Ipom. spp. | Mentha piper. | Cynodon dact. (seed) | Sinapis alba |
| (Br, Br, bicyclic, NH–C=O) | 3.0 POST | 95 | 70 | 95 | 40 | — | — |
| (O, bicyclic, N$^x$=N) | 3.0 PRE | 95 | — | — | — | — | 90 |
| | 3.0 POST | 100 | 60 | 100 | 100 | — | — |
| (O, Br, bicyclic, N–O$^x$=N) | 3.0 POST | — | 30 | 100 | 40 | — | — |
| (Br, Br, bicyclic, N–O$^x$=N) | 3.0 PRE | 80 | — | — | — | — | 80 |
| | 3.0 POST | 85 | 40 | 60 | 95 | — | — |
| (H$_3$C–C$_6$H$_4$–NH, Cl, bicyclic, N$^x$=N) | 3.0 PRE | 80 | — | — | — | — | 100 |
| | 3.0 POST | 100 | 75 | 100 | 100 | — | — |

| | | Test plants and % damage | | | | | |
|---|---|---|---|---|---|---|---|
| Compound | kg/ha | Lolium mult. | Galium apar. | Ipom spp. | Mentha piper. | Cynodon dact. (seed) appln. rate 2 kg/ha | Sinapis alba |
| (H$_3$C–C$_6$H$_4$–NH, Br, bicyclic, N$^x$=N) | 3.0 PRE | 95 | — | — | — | — | 100 |
| | 3.0 POST | 100 | 80 | 100 | 100 | 100 | — |

| | | | | | | | |
|---|---|---|---|---|---|---|---|
| 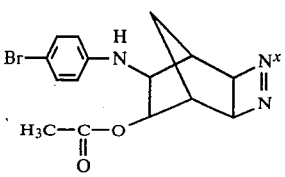 | 3.0 PRE | 80 | — | — | — | — | 100 |
| | 3.0 POST | 100 | 65 | 85 | 95 | — | — |
| 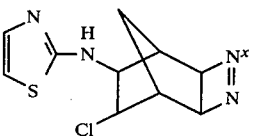 | 3.0 POST | 100 | 80 | 80 | 100 | — | — |
| 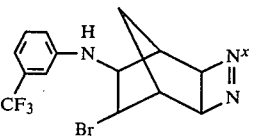 | 3.0 PRE | 100 | — | — | — | — | 95 |
| | 3.0 POST | 100 | 90 | 100 | 95 | — | — |
| 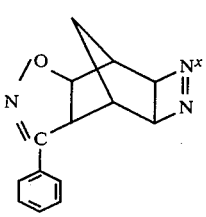 | 3.0 PRE | 100 | — | — | — | — | 90 |
| | 3.0 POST | 100 | 95 | 100 | 75 | 100 | — |

$^x$dissolved in dimethylformamide before application

EXAMPLE 14

20 parts by weight of compound 1 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 15

3 parts by weight of compound 2 is intimately mixed with 97 parts by weight of particulate kaolin. A dust is obtained containing 3% by weight of the active ingredient.

EXAMPLE 16

30 parts by weight of compound 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 17

40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 18

20 parts of compound 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

EXAMPLE 19

90 parts by weight of compound 1 is mixed with 10 parts by weight of N-methyl-α-pyrrolidone. A mixture is obtained which is suitable for application in the form of very fine drops.

EXAMPLE 20

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 21

20 parts by weight of compound 1 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 22

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

We claim:

1. A compound of the formula

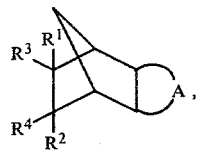

where $R^3$ and $R^4$ are either individual radicals or together form the radical $(B)_n$, A denotes the radical

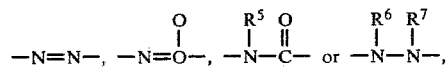

B denotes the radical

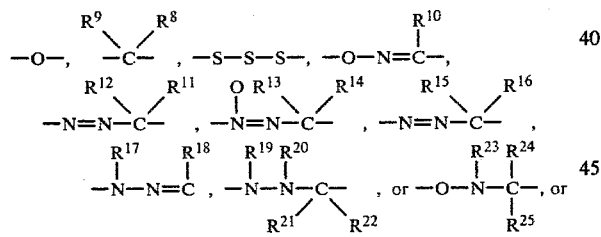

when A is

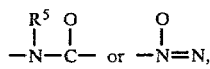

B also denotes the radical

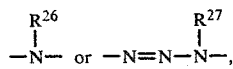

n is one of the integers 0 and 1, $R^1$ to $R^{27}$ are identical or different and each denotes hydrogen, with the exception of $R^3$ and $R^4$, or alkyl, with the exception of $R^6$ and $R^7$ and with the proviso that $R^3$ and $R^4$ do not simultaneously denote alkyl, alkenyl or alkynyl of 1 to 30 carbon atoms, phenyl, naphthyl, or the aromatic radical

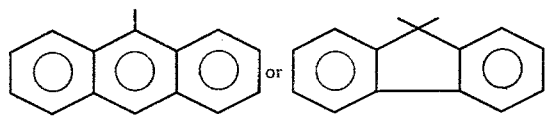

a heterocyclic radical selected from the group consisting of

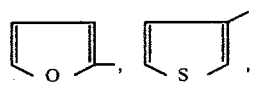

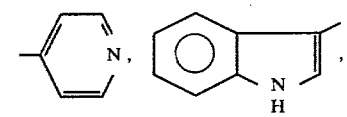

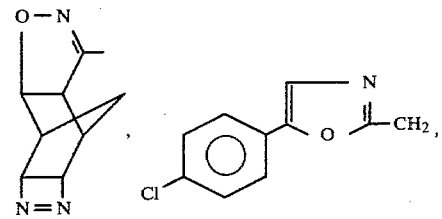

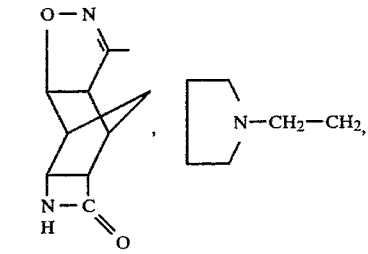

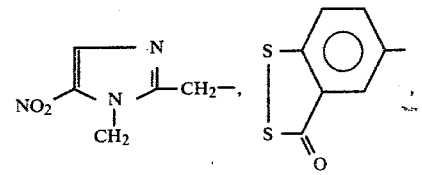

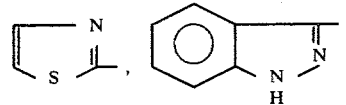

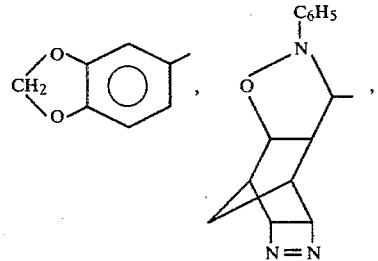

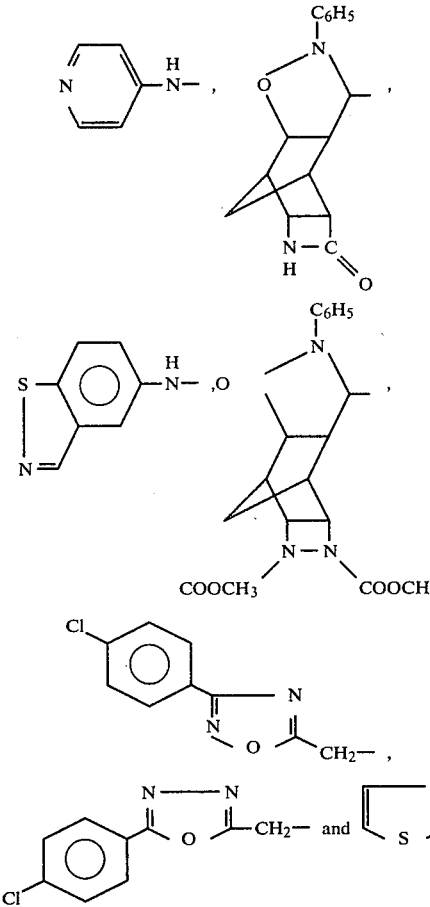

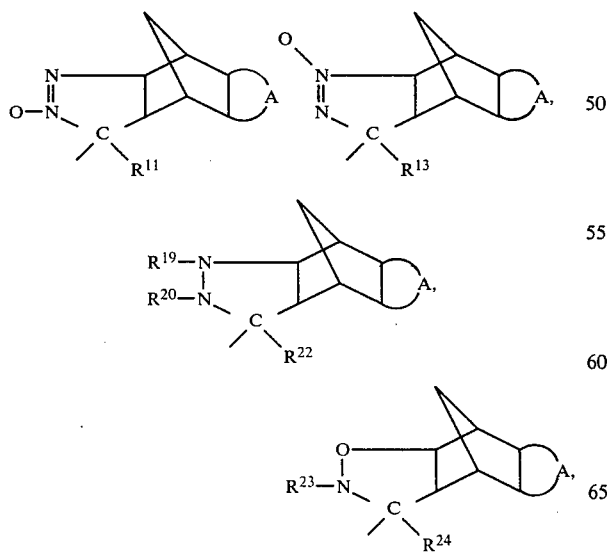

aralkyl or alkyl substituted by one of said heterocyclic radicals; the abovementioned radicals $R^1$ to $R^{27}$, apart from hydrogen, being unsubstituted or mono- or polysubstituted by halogen, azide, cyanide, cyanate, thiocyanate, —OH, —SH, —NO$_2$, further, $R^1$ and $R^7$ are also selected from the group consisting of halogen, —N$_3$, —CN, —OCN, —SCN, —OH, —SH, —NO$_2$, —NH$_2$, —NO, $$-\overset{H}{N}-OH, \quad -\overset{H}{N}-OAlk(Ar),$$

—N(H,Alk)—N(H,Alk,Ar)$_2$, —COOH or —SO$_3$H or salts thereof, —SO$_2$Cl, Alk(Ar)—O—,

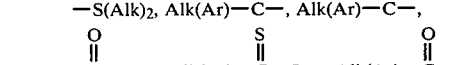

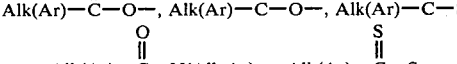

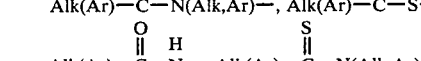

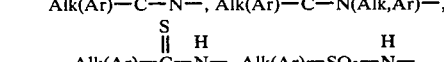

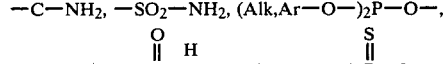

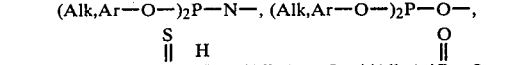

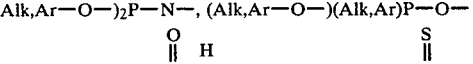

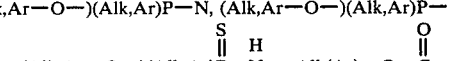

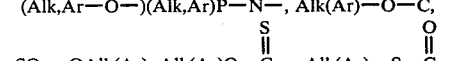

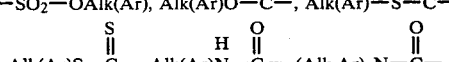

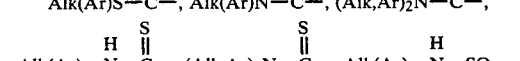

(Alk,Ar)$_2$N—SO$_2$—, Alk(Ar)—N=N—, =N—OH,

=O, =N—Oalk(Ar), =S, =NH, =NAlk(Ar), $$\equiv N, \quad -\overset{H}{N}-OH, \quad -\overset{H}{N}-OAlk(Ar),$$

—N(H,Alk)—N(H,Alk,Ar)$_2$, =N—N(H,Alk,Ar)$_2$,

=C(H,Alk,Ar)$_2$, Alk(Ar)—$\overset{\overset{S}{\|}}{C}$—$\overset{H}{N}$—, ClSO$_2$—

—SO$_2$—OAlk(Ar)—, haloalkyl, haloalkoxy, haloalkylmercapto or the radicals

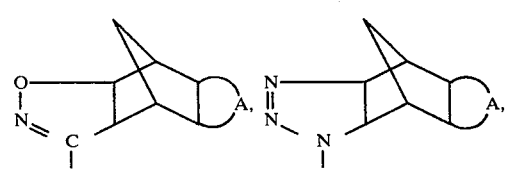

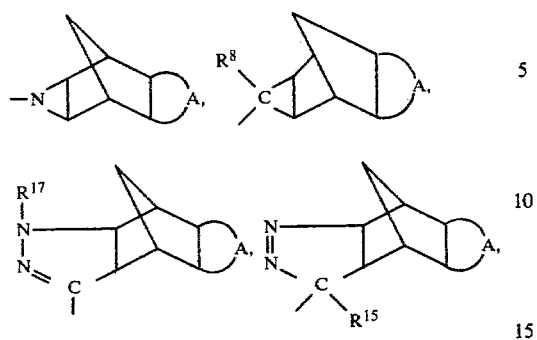
and $R^1$ and $R^3$ together, or $R^2$ and $R^4$ together, also denote =O, =S, =NH, =NAlk(Ar), =N—OH, =N—OAlk(Ar), =C(H,Alk,Ar)$_2$,
$$=N-\overset{H}{N}-Alk(Ar)$$
=N—N(H,Alk,Ar), wherein Alk is alkyl of 1–30 carbon atoms and Ar is phenyl, naphthyl,
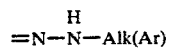
2. A compound selected from the group consisting of compounds of the formulae
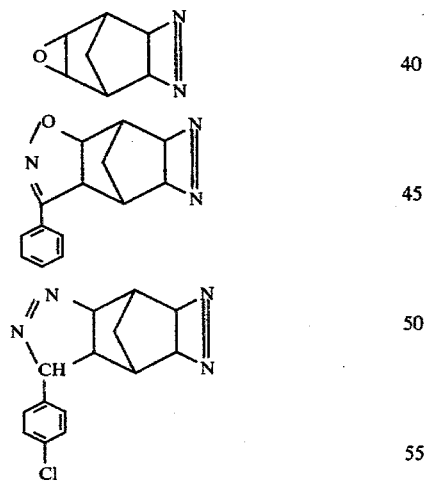
and
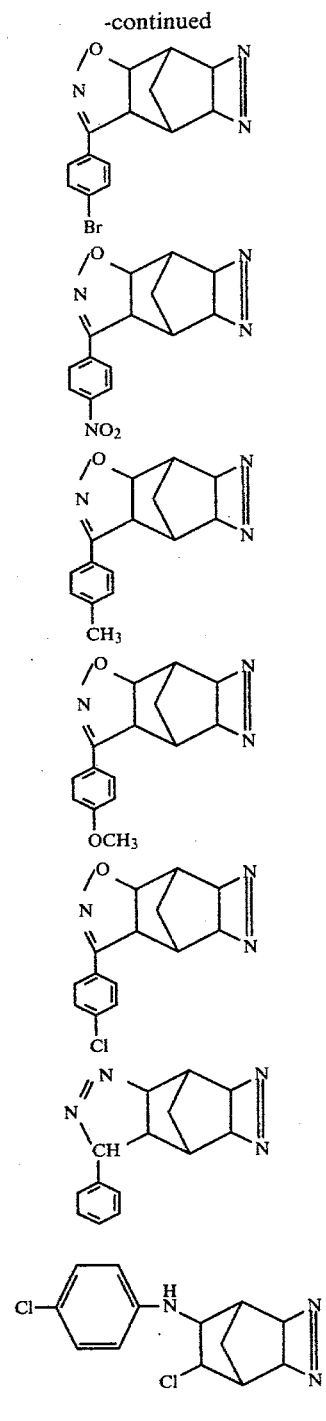
* * * * *